US008603967B2

(12) United States Patent
Yoshida et al.

(10) Patent No.: US 8,603,967 B2
(45) Date of Patent: *Dec. 10, 2013

(54) CARRIER PEPTIDE FRAGMENT AND USE THEREOF

(75) Inventors: Tetsuhiko Yoshida, Tsukuba (JP); Nahoko Kobayashi, Tsukuba (JP); Mikio Niwa, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/386,539

(22) PCT Filed: Jul. 28, 2010

(86) PCT No.: PCT/JP2010/062693
§ 371 (c)(1),
(2), (4) Date: Jan. 23, 2012

(87) PCT Pub. No.: WO2011/013700
PCT Pub. Date: Feb. 3, 2011

(65) Prior Publication Data
US 2012/0122210 A1    May 17, 2012

(30) Foreign Application Priority Data

Jul. 29, 2009 (JP) ................................ 2009-177103

(51) Int. Cl.
*A61K 38/04* (2006.01)
*C07K 7/00* (2006.01)

(52) U.S. Cl.
USPC ............ 514/1.2; 514/21.5; 530/300; 530/327

(58) Field of Classification Search
None
See application file for complete search history.

(56) References Cited

U.S. PATENT DOCUMENTS

| | | | |
|---|---|---|---|
| 4,867,975 | A | 9/1989 | Gelb, Jr. |
| 6,037,521 | A | 3/2000 | Sato et al. |
| 6,340,583 | B1 | 1/2002 | Yan et al. |
| 6,403,353 | B1 | 6/2002 | Yan et al. |
| 6,423,684 | B1 | 7/2002 | Mochly-Rosen et al. |
| 2003/0125242 | A1 | 7/2003 | Rosenecker et al. |
| 2003/0166215 | A1 | 9/2003 | Yan et al. |
| 2003/0229202 | A1 | 12/2003 | Guo et al. |
| 2004/0175751 | A1 | 9/2004 | Yan et al. |
| 2004/0186052 | A1 | 9/2004 | Iyer et al. |
| 2004/0226056 | A1 | 11/2004 | Roch et al. |
| 2006/0100134 | A1 | 5/2006 | Guo et al. |
| 2006/0166917 | A1 | 7/2006 | Lindeman et al. |
| 2006/0270834 | A1 | 11/2006 | Kanno |
| 2007/0065941 | A1 | 3/2007 | Kondo et al. |
| 2008/0076145 | A1 | 3/2008 | Cummings et al. |
| 2009/0253618 | A1 | 10/2009 | Kanno et al. |
| 2010/0297758 | A1 | 11/2010 | Yoshida et al. |
| 2012/0035112 | A1 | 2/2012 | Yoshida et al. |
| 2012/0122225 | A1 | 5/2012 | Kobayashi et al. |
| 2012/0208752 | A1 | 8/2012 | Yoshida et al. |
| 2013/0005034 | A1 | 1/2013 | Yoshida et al. |
| 2013/0079273 | A1 | 3/2013 | Yoshida et al. |

FOREIGN PATENT DOCUMENTS

| | | |
|---|---|---|
| EP | 1 918 297 A1 | 5/2008 |
| JP | A-7-132033 | 5/1995 |
| JP | A-9-323928 | 12/1997 |
| JP | A-2001-199997 | 7/2001 |
| JP | A-2003-137899 | 5/2003 |
| JP | A-2004-357543 | 12/2004 |
| JP | A-2005-154338 | 6/2005 |
| JP | A-2005-330206 | 12/2005 |
| JP | B2-3854995 | 12/2006 |
| JP | A-2007-145761 | 6/2007 |
| JP | A-2007-159429 | 6/2007 |
| JP | A-2009-209064 | 9/2009 |
| JP | A-2011-016763 | 1/2011 |
| WO | WO 02/18572 A2 | 3/2002 |
| WO | WO 02/077171 A2 | 10/2002 |
| WO | WO 03/076561 A2 | 9/2003 |
| WO | WO 2004/056854 A1 | 7/2004 |
| WO | WO 2005/086800 A2 | 9/2005 |
| WO | WO 2007/010989 A1 | 1/2007 |
| WO | WO 2007/149293 A2 | 12/2007 |
| WO | WO 2008/008569 A2 | 1/2008 |
| WO | WO 2009/093692 A1 | 7/2009 |
| WO | WO 2010/117078 A1 | 10/2010 |
| WO | WO 2010/117079 A1 | 10/2010 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Goyal, et al., "Phosphorylation-dependent Regulation of Unique Nuclear and Nucleolar Localization Signals of LIM Kinase 2 in Endothelial Cells," *The Journal of Biological Chemistry*, vol. 281, No. 35, pp. 25223-25230, Sep. 1, 2006.
Hilton, et al., "Twenty proteins containing a C-terminal SOCS box form five structural classes," *Proc. Natl. Acad. Sci. USA*, vol. 95, pp. 114-119, Jan. 1998.

(Continued)

*Primary Examiner* — Julie Ha
*Assistant Examiner* — Li Ni Komatsu
(74) *Attorney, Agent, or Firm* — Oliff & Berridge, PLC

(57) ABSTRACT

A method for transferring a foreign substance includes the steps of: preparing a construct for transferring a foreign substance that contains a carrier peptide fragment including either the amino acid sequence KKRTLRKNDRKKR (SEQ ID NO. 1) or an amino acid sequence formed by the substitution, deletion, and/or addition (insertion) of 1, 2, or 3 amino acid residues in the amino acid sequence, and a foreign substance of interest that is bonded to the N-terminus and/or C-terminus of the carrier peptide fragment; supplying the construct for transferring a foreign substance to a test sample that contains a target eukaryotic cell; and incubating the test sample that has been supplied with the construct for transferring a foreign substance to thereby transfer the construct into the eukaryotic cell in the test sample.

5 Claims, 2 Drawing Sheets

(56) References Cited

OTHER PUBLICATIONS

Oct. 5, 2010 International Search Report issued in International Patent Application No. PCT/JP2010/062693 (with translation).
Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.
Boursnell et al., "Sequences of the Nucleocapsid Genes from Two Strains of Avian Infectious Bronchitis Virus," J. Gen. Virol., vol. 66, pp. 573-580, 1985.
Cserpán et al., "The Mechanism of Nuclear Transport of Natural or Artificial Transport Substrates in Digitonin-Permeabilized Cells," Journal of Cell Science, vol. 108, pp. 1849-1861, 1995.
Eiges et al., "Establishment of Human Embryonic Stem Cell-Transfected Clones Carrying a Marker for Undifferentiated Cells," Current Biology, vol. 11, pp. 514-518, 2001.
Emmott et al., "Nucleolar Targeting: The Hub of the Matter," European Molecular Biology Organization, vol. 10, No. 3, pp. 231-238, 2009.
Fang et al., "Selection of and Recombination between Minor Variants Lead to the Adaptation of an Avian Coronavirus to Primate Cells," Biochemical and Biophysical Research Communications, vol. 336, pp. 417-423, 2005.
Futaki et al., "Intracellular Protein Delivery Using Membrane-Permeable Peptides," Seibutsu to Kagaku, vol. 43, No. 10, pp. 649-653, 2005, with English-language translation.
Kamura et al., "The Elongin BC Complex Interacts with the Conserved SOCS-Box Motif Present in Members of the SOCS, Ras, WD-40 Repeat, and Ankyrin Repeat Families," Genes & Development, vol. 12, pp. 3872-3881, 1998.
Kamura et al., "VHL-Box and SOCS-Box Domains Determine Binding Specificity for Cul2-Rbx1 and Cul5-Rbx2 Modules of Ubiquitin Ligases," Genes & Development, vol. 18, pp. 3055-3065, 2004.
Kang et al., "The Precursor of Alzheimer's Disease Amyloid A4 Protein Resembles a Cell-Surface Receptor," Nature, vol. 325, pp. 733-736, Feb. 19, 1987.
Kile et al., "The Suppressors of Cytokine Signalling (SOCS)," Cellular and Molecular Life Sciences, vol. 58, pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Liu et al., "Rack1 Competes with HSP90 for Binding to HIF-1α and is Required for $O_2$-Independent and HSP90 Inhibitor-Induced Degradation of HIF-1α," Molecular Cell, vol. 25, pp. 207-217, Jan. 26, 2007.
Liu et al., "Calcineurin Promotes Hypoxia-Inducible Factor 1α Expression by Dephosphorylating RACK1 and Blocking Rack1 Dimerization," Journal of Biological Chemistry, vol. 282, No. 51, pp. 37064-37073, Dec. 21, 2007.
Liu et al., "Rack1 vs. HSP90: Competition for HIF-1α Degradation vs. Stablization," Cell Cycle, vol. 6, No. 6, pp. 656-659, Mar. 15, 2007.
Martoglio et al., "Signal Sequences: More than just Greasy Peptides," Trends in Cell Biology, vol. 8, pp. 410-415, Oct. 1998.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.
NCBI database Accession No. Q1M2X0, p. 1, accessed Nov. 7, 2012.
Pokorska et al., "The Analysis of the Transcriptional Activator PrnA Reveals a Tripartite Nuclear Localisation Sequence," J. Mil. Biol., vol. 298, pp. 585-596, 2000.
Reed et al., "Delineation and Modelling of a Nucleolar Retention Signal in the Coronavirus Nucleocapsid Protein," Traffic, vol. 7, pp. 833-848, 2006.
Sugaya et al., "Practical Issues in Stem Cell Therapy for Alzheimer's Disease," Curr. Alzheimer Res., vol. 4, No. 4, pp. 370-377, 2007 (Abstract Only).
Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Yu et al., "Selective Assembly of HIV-1 Vif-Cul5-ElonginB-ElonginC E3 Ubiquitin Ligase Complex through a Novel SOCS Box and Upstream Cysteines," Genes & Development, vol. 18, pp. 2867-2872, 2004.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510 (with translation).
Oct. 5, 2010 International Search Report issued in International Patent Application No. PCT/JP2010/062691 (with translation).
Jan. 18, 2011 International Search Report issued in International Patent Application No. PCT/JP2010/069165.
Jul. 19, 2011 International Search Report issued in International Application No. PCT/JP2011/062809.
Jun. 12, 2012 International Preliminary Report on Patentability and Written Opinion issued in International Patent Application No. PCT/JP2010/069165.
Jan. 8, 2013 International Preliminary Report on Patentability and Written Opinion issued in International Application No. PCT/JP2011/062809.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,582.
Jan. 31, 2013 Office Action issued in U.S. Appl. No. 13/258,788.
Feb. 22, 2013 Office Action issued in U.S. Appl. No. 13/386,582.
Apr. 17, 2013 Office Action issued in U.S. Appl. No. 13/503,220.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.
Dieterlen-Lievre, "On the Origin of Haemopoietic Stem Cells in the Avian Embryo: An Experimental Approach," J. Embryol. exp. Morph., vol. 33, No. 3, pp. 607-619, 1975.
Aug. 7, 2013 Office Action issued in U.S. Appl. No. 13/258,788.
Aug. 6, 2013 Office Action issued in U.S. Appl. No. 13/386,582.
Selkoe, "Normal and Abnormal Biology of the Beta-Amyloid Precursor Protein," Annu. Rev. Neurosci., vol. 17, pp. 489-517, 1994.
Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.
Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.
Kwak, "Studies on the Novel Function of Amyloid Precursor Protein in Glial Differentiation of Neural Stem Cells," Dissertation, pp. 1-173, 2006.
Oct. 16, 2013 Office Action issued in U.S. Appl. No. 13/701,747.

* cited by examiner

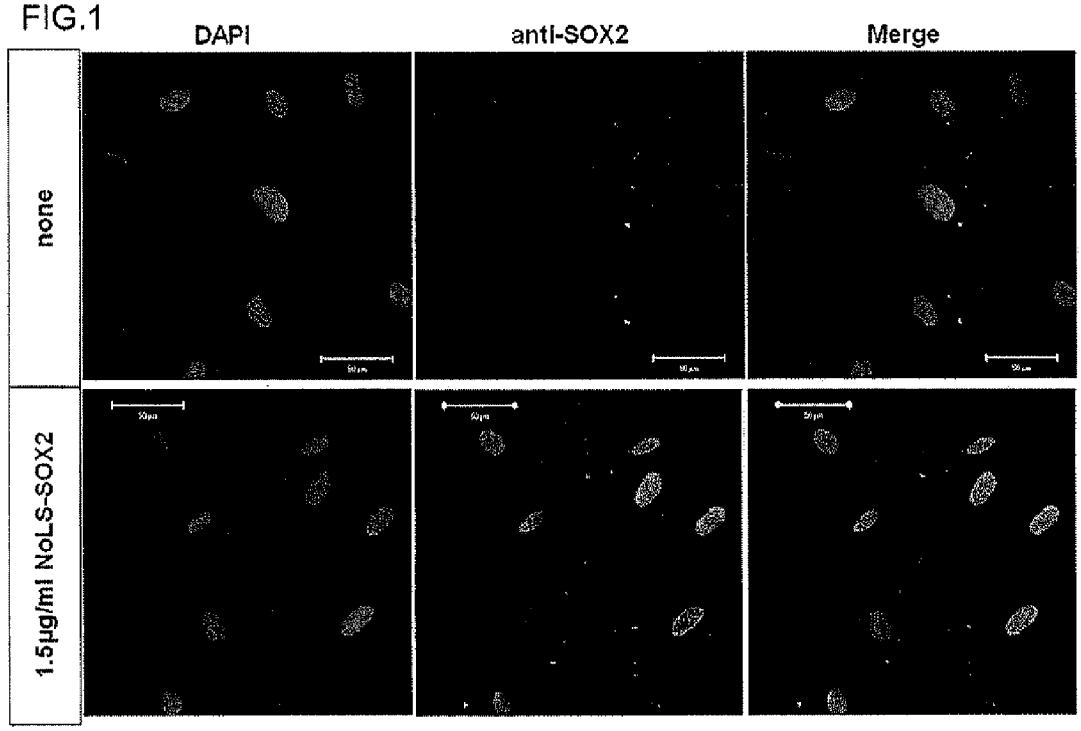

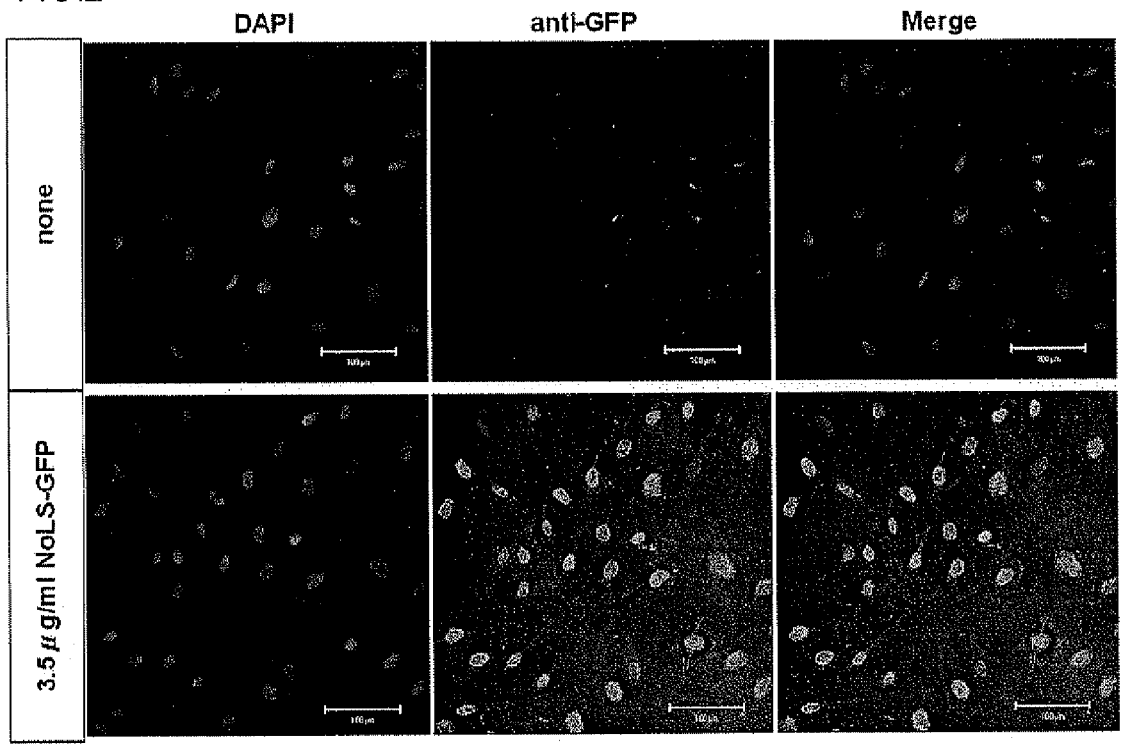

CARRIER PEPTIDE FRAGMENT AND USE THEREOF

TECHNICAL FIELD

The present invention relates to a method for transferring (carrying) a foreign substance from outside a eukaryotic cell into the cell, and a carrier peptide fragment used in the method.

The present application claims priority on the basis of Japanese Patent Application No. 2009-177103 filed on 29 Jul. 2009, and the entire content of the domestic application is incorporated into the description of the present application by reference.

BACKGROUND ART

Polypeptides and other foreign substances, particularly biologically active substances, are transferred into the cells of humans and other mammals, etc., (eukaryotic cells) to change the characteristics or to improve and enhance the function of the cells (as well as the tissues and organs comprising the cells).

For example, Patent Document 1 discloses a transcellular carrier peptide for transferring polypeptide, DNA or another foreign substance into a cell. This patent indicates that a polypeptide, DNA, or other biologically active substance can be transferred into a cell with high efficiency by using a carrier peptide conjugate comprising a transcellular carrier peptide linked to a xenogenic polypeptide, DNA, and the like.

Still, a method is needed for changing the characteristics and improving (or enhancing) the function of the cells by easily transferring a full-length polypeptide with a relatively large molecular weight as the foreign substance (biologically active substance) to be transferred into a target cell without the use of special equipment.

Alternatively, in place of transferring a polypeptide or a full-length protein, a method is needed wherein the focus is placed on the specific function of the polypeptide, and a partial amino acid sequence that is the minimum unit capable of expressing that function, i.e., an amino acid sequence (foreign substance) constituting a peptide motif, is transferred efficiently into the cell.

PRIOR ART

Patent Document

Patent Document 1: Japanese Patent Publication No. 3854995
Patent Document 2: WO 2007/010989

Non-Patent Document

Non-Patent Document 1: JOURNAL OF BIOLOGICAL CHEMISTRY, Vol. 281, No. 35, 2006, pages 25223 to 25230
Non-Patent Document 2: PNAS, Vol. 95, 1998, pages 114 to 119

DISCLOSURE OF THE INVENTION

As noted in abovementioned Patent Document 1, however, previously well-known transcellular carrier peptides (e.g., transcellular carrier peptides originating in HIV and *Drosophila*) are not considered sufficiently capable of transferring a foreign substance with a relatively large number molecular weight such as a polypeptide (protein), DNA, and the like, and a transcellular carrier peptide that can pass through the cell membrane more efficiently and transfer a foreign substance into the cytoplasm is needed. For example, adding a specific amino acid sequence to the C-terminus of a prior art transcellular carrier peptide has successfully achieved a slight increase in cell membrane permeability through the technology disclosed in abovementioned Patent Document 1, but the result is still insufficient to meet this need.

Hence, the prevent invention was created in response to this need, and an object of the present invention is to provide a carrier peptide (fragment) that has an amino acid sequence different from previously known transcellular carrier peptides, and that is a carrier peptide fragment with a relatively short chain length that can efficiently transfer a foreign substance with a relatively large molecular weight into a cell. Another object of the present invention is to provide a method that uses this carrier peptide fragment to pass a variety of foreign substances through the cell membrane from outside and transfer the same into a target cell. Moreover, the present invention provides a construct for transferring a foreign substance that has been configured to comprise the carrier peptide fragment disclosed herein and a foreign substance. Furthermore, the present invention provides a cell, organ, or other biological tissue obtained by transferring the construct comprising the carrier peptide fragment disclosed herein and a foreign substance into the cytoplasm (including into the nucleus) thereof.

The inventors conducted various investigations of peptides (or amino acid sequences constituting parts thereof (i.e., motifs with identified functions)) with previously identified amino acid sequences as peptides having some kind of intracellular function, and they discovered an amino acid sequence that can be preferably used as the abovementioned carrier peptide (fragment) despite having a relatively short chain, thus completing the present invention.

One method provided by the present invention is a process for transferring (carrying) a foreign substance of interest from outside (i.e., outside the cell membrane) of eukaryotic cells (in particular, various animal cells typified by human and other mammalian cells that do not have a cell wall) at least into the cytoplasm (preferably, into the nucleus as well) of the cell.

More specifically, the method for transferring a foreign substance disclosed herein comprises the steps of:

preparing a construct for transferring a foreign substance that contains a carrier peptide fragment comprising either the amino acid sequence KKRTLRKNDRKKR (SEQ ID NO: 1) or an amino acid sequence formed by the substitution, deletion, and/or addition (insertion) of 1, 2, or 3 amino acid residues in the amino acid sequence, and a foreign substance of interest that is bonded to the N-terminus and/or C-terminus of the carrier peptide fragment;

supplying the abovementioned construct for transferring a foreign substance to a test sample that contains a target eukaryotic cell (typically a culture containing the cell); and incubating the abovementioned test sample that has been supplied with the abovementioned construct for transferring a foreign substance (i.e., maintaining the test sample under conditions enabling survival of the target cell for a predetermined time period) to thereby transfer the construct into the eukaryotic cell in the abovementioned test sample.

The term "foreign substance" used herein refers to an inorganic or organic compound that is capable of bonding either directly or indirectly via a suitable linker to the N-terminus or C-terminus of the abovementioned carrier peptide fragment, and that has a molecular size and chemical properties enabling transfer thereof into a eukaryotic cell.

The inventors prepared a construct containing the amino acid sequence of abovementioned SEQ ID NO: 1, which is known as a nucleolar localization signal (hereinafter abbreviated as "NoLS") as disclosed in abovementioned Non-Patent Document 1, and a foreign substance of interest, and when they supplied the construct to eukaryotic cells in culture, they discovered that the construct can pass through the cell membrane of a target eukaryotic cell with high efficiency, thus completing the present invention.

More specifically, the method for transferring a foreign substance of the present invention with the abovementioned configuration enables a foreign substance of interest to pass through the cell membrane from outside a eukaryotic cell (outside the cell membrane) and be transferred into the cytoplasm (more preferably, pass through the nuclear membrane and into the nucleus) with high efficiency by preparing a construct for transferring a foreign substance by bonding a foreign substance of interest (typically, an organic chemical such as a polypeptide, nucleic acid, dye, drug, etc.) either directly or indirectly via a suitable linker to the N-terminus and/or C-terminus of the abovementioned peptide fragment and supplying that construct to a test sample containing a target eukaryotic cell (typically a culture containing the cells) (in other words, by adding the construct to living eukaryotic cells).

In one preferred mode of the method for transferring a foreign substance disclosed herein, the abovementioned foreign substance is characterized in that it is any organic compound selected from a group consisting of polypeptides, nucleic acids, dyes, and drugs. A construct prepared so that it contains this type of organic compound enables the efficient transfer thereof into a target cell.

Herein the term "polypeptide" refers to a polymer having a configuration wherein a plurality of amino acids are linked by peptide bonds, but it is not limited by the number of peptide bonds (i.e., amino acid residue). In other words, the term polypeptide encompasses compounds generally called peptides with about 10 or more but fewer than 300 amino acid residues, and compounds generally called proteins (typically, a macromolecular compound comprising 300 or more amino acid residues). In practice, no fine distinction is made in the field between polypeptides and proteins, and in this description polymers (including oligomers) comprising a plurality of amino acid residues fall under the blanket term of polypeptide.

Moreover, the term "nucleic acid" used herein refers to a nucleotide polymer and includes DNA and RNA. The term is not limited by the number of nucleotides. Moreover, in one preferred embodiment of the method for transferring a foreign substance disclosed herein, the abovementioned foreign substance is a polypeptide, and can be a polypeptide with a relatively large molecular weight (number of amino acid residues). For example, a polypeptide with 100 or more amino acid residues (e.g., about 100 to 1000, typically about 100 to 600, e.g., about 200 to 500) can be used as the foreign substance. Preferably the foreign substance is a mature polypeptide originating in any biological species, or a precursor polypeptide thereof (i.e., a pre-form polypeptide or pre-pro-form polypeptide in relation to the mature polypeptide), and the construct for transferring a foreign substance is provided as a synthetic polypeptide containing an amino acid sequence corresponding to the mature polypeptide or precursor polypeptide thereof as the foreign substance and the amino acid sequence of the carrier peptide fragment. The term synthetic polypeptide herein encompasses both polypeptides that are biosynthesized by so-called genetic engineering techniques, and polypeptides obtained by chemical synthesis (for example, use of a commercially available peptide synthesizer). The method of this embodiment enables a polypeptide of interest (i.e., the amino acid sequence constituting the polypeptide) to be transferred into the target cell in the form of the abovementioned synthetic peptide. For example, a synthetic polypeptide or precursor polypeptide thereof constituting between 100 and 1000 amino acid residues can be transferred into a target cell thereby.

In another preferred embodiment of the method for transferring a foreign substance disclosed herein, the target eukaryotic cell to which the abovementioned construct for transferring a foreign substance is to be transferred is characterized in that it is a cell of human or nonhuman mammalian origin (for example, somatic cells and germ cells of various morphologies, and stem cells that include induced pluripotent stem cells (so-called iPS cells) and ES cells).

The present invention enables the transfer of a foreign substance of interest having a designated function into a human or nonhuman mammalian cell (for example, a somatic cell such as a skin cell or nerve cell, etc., a somatic stem cell, an induced pluripotent stem cell, or ES cell). For example, by targeting a stem cell such as an ES cell or iPS cell, the stem cell can be transformed in response to the transferred foreign substance (polypeptide, etc.) and, for example, can differentiate into a specific cell type (nerve cell, bone cell, muscle cell, skin cell, etc.).

Moreover, the present invention provides a construct artificially prepared in order to transfer a foreign substance of interest from outside a eukaryotic cell (in particular, various animal cells typified by human and other mammalian cells that do not have a cell wall) at least into the cytoplasm (preferably, also into the nucleus) of the cell for realizing the abovementioned object.

In other words, the construct for transferring a foreign substance disclosed herein contains a carrier peptide fragment comprising either the amino acid sequence consisting of KKRTLRKNDRKKR (SEQ ID NO: 1) or an amino acid sequence formed by the substitution, deletion and/or addition (insertion) of 1, 2, or 3 amino acid residues in the amino acid sequence, and a foreign substance of interest that is bonded to the N-terminus and/or C-terminus of the carrier peptide fragment.

A foreign substance of interest can be transferred effectively to a target cell by implementing the above-described transfer method for a foreign substance of the present invention utilizing this construct. In addition, cells to which the foreign substance has been transferred, as well as organs and other body tissues comprising cells that contain the foreign substance can be obtained thereby.

Preferably, as noted above, the abovementioned foreign substance is any organic compound selected from a group consisting of polypeptides, nucleic acids, dyes, and drugs.

Moreover, most preferably the abovementioned foreign substance is a polypeptide and, for example, a polypeptide with 100 or more amino acid residues (for example, about 100 to 1000, typically about 100 to 600) can be used as the foreign substance. Moreover, one preferred example of the construct for transferring a foreign substance the foreign substance is a mature polypeptide originating in any biological species or a precursor polypeptide thereof, and the construct is configured as a synthetic polypeptide containing an amino acid sequence (for example, constituting between 100 and 1000 amino acid residues) corresponding to the mature polypeptide or precursor polypeptide thereof as the foreign substance, and the amino acid sequence of the carrier peptide fragment.

BRIEF EXPLANATION OF THE DRAWINGS

FIG. 1 shows fluorescence micrographs obtained by adding the polypeptide of one example (Sample No. 1: NoLS-SOX2 fusion protein) to a liquid culture medium containing human neonate fibroblasts to reach a concentration of 1.5 µg/mL with respect to the liquid culture medium, culturing the cells for 2 hours, and detecting the presence or absence of the polypeptide of Sample No. 1 in cells by a fluorescence antibody technique using an antigen-antibody reaction. The photos in FIG. 1 are divided into upper and lower rows, with the top showing a control region to which the polypeptide of Sample No. 1 was not added, and the bottom showing the test region to which the polypeptide of Sample No. 1 (NoLS-SOX2 fusion protein) was added. FIG. 1 is also divided into three columns left to right, with the area on the left showing a plot produced by nuclear staining using DAPI (4',6-diamidino-2-phenylindole), the center area showing a fluorescent state due to the presence of a fluorescent dye-labeled antibody (secondary antibody), and the area on the right showing the plot produced by nuclear staining using DAPI overlain (merged) with the fluorescent state due to the presence of the fluorescent dye-labeled antibody. The scale represents 50 µm.

FIG. 2 is a fluorescence micrograph obtained by adding the polypeptide of one example (Sample No. 2: NoLS-GFP fusion protein) to a liquid culture medium containing human neonate fibroblasts to reach a concentration of 3.5 µg/mL with respect to the liquid culture medium, culturing the cells for 2 hours, and detecting the presence or absence of the polypeptide of Sample No. 2 in cells by a fluorescence antibody technique using an antigen-antibody reaction. The photos in FIG. 2 are divided into upper and lower rows, with the top showing a control region to which the polypeptide of Sample No. 2 was not added, and the bottom showing the test region to which the polypeptide of Sample No. 2 (NoLS-GFP fusion protein) was added. FIG. 2 is also divided into three columns left to right, with the area on the left showing a plot produced by nuclear staining using DAPI, the center area showing a fluorescent state due to the presence of a fluorescent dye-labeled antibody (secondary antibody), and the area on the right showing the plot produced by nuclear staining using DAPI overlain (merged) with the fluorescent state due to the presence of the fluorescent dye-labeled antibody. The scale represents 100 p.m.

BEST MODE FOR CARRYING OUT THE INVENTION

Preferred embodiments of the invention of the present invention are described below. It should also be noted that matters necessary for carrying out the invention beyond those specifically stated in the present description (for example, general matters related to peptide synthesis and cell culture) are understood to be matters of design based on prior art in fields such as medicine, pharmacology, organic chemistry, biochemistry, genetic engineering, protein synthesis, molecular biology, hygiene, and the like.

Moreover, the present invention can be carried out on the basis of the details disclosed herein and common technical knowledge in the fields. It should also be noted that in each instance the amino acids are expressed in the following explanation by single letter codes (by 3-letter codes in the sequence listings) based on the nomenclature for amino acids in the IUPAC-IUB guidelines. It should also be noted that in this description the term "amino acid residue" includes the N-terminal amino acid and C-terminal amino acid unless specifically stated otherwise.

The term "carrier peptide fragment" used herein is a sequence defined (comprehended) by the amino acid sequence of abovementioned SEQ ID NO: 1, and is an amino acid sequence that exhibits cell membrane permeability (more preferably nuclear translocation capability (i.e., nuclear membrane permeability)) in eukaryotic cells.

The specific amino acid sequence disclosed in SEQ ID NO: 1 herein is an NoLS corresponding to a partial sequence (i.e., a motif) comprising a total of 13 amino acid residues from residue 491 to residue 503 of LIM kinase 2 (see abovementioned Non-Patent Document 1), which is present in human endothelial cells and is a type of protein kinase involved in intracellular signal transduction, and it is also a sequence newly discovered by the inventors to exhibit excellent cell membrane permeability. In other words, even though this is a short chain peptide fragment of 13 amino acid residues, it can transfer a relatively high molecular weight foreign substance (for example, a molecular weight of about 100 to 200,000 typically 1,000 to 100,000) from outside a cell into the cytoplasm.

The "carrier peptide fragment" disclosed herein is typically a sequence identical to the amino acid sequence represented by SEQ ID NO: 1, but in addition thereto, it encompasses an amino acid sequence formed by the substitution, deletion and/or addition (insertion) of one or several (typically 2 or 3) amino acid residues therein without the loss of cell membrane permeability. In other words, such a slightly modified sequence can be easily used by a person skilled in the art on the basis of the information disclosed herein, and therefore is encompassed by the term "carrier peptide fragment" as a technical concept disclosed herein. Typical examples include a sequence produced by so-called conservative amino acid replacement wherein one or several (typically 2 or 3) amino acid residues in the amino acid sequence of SEQ ID NO: 1 are conservatively replaced (for example, a sequence wherein a basic amino acid residue is replaced by a different basic amino acid residue), or a sequence wherein one or several (typically 2 or 3) amino acid residues are added (inserted) to or deleted from the designated amino acid sequence.

The construct for transferring a foreign substance disclosed herein is a construct that can be designed and configured by bonding (linking), either directly or indirectly via a suitable linker, a desired foreign substance to the N-terminus and/or C-terminus of the abovementioned carrier peptide fragment. For example, if the foreign substance is a polypeptide, the peptide chain can be designed to contain the amino acid sequence constituting the polypeptide and the amino acid sequence constituting the carrier peptide fragment, and then the intended construct for transferring a foreign substance of interest can be prepared by biosynthesis or chemical synthesis of the peptide chain. Moreover, the construct for transferring a foreign substance can be configured by directly or indirectly bonding a nucleic acid such as various types of DNA or RNA, or an organic compound that acts as a dye (for example, a fluorescent compound such as FITC) or that acts as a drug (for example a nucleic acid-based anticancer drug such as 5-fluorouracil (5FU) or an antiviral drug such as azidothymidine (AZT)) to the N-terminus and/or C-terminus of the above carrier peptide fragment by various prior art and publicly known chemical methods.

It should also be noted that when the foreign substance is a polypeptide, the polypeptide (amino acid sequence) to be used is not particularly limited herein. A polypeptide or protein with a relatively large number of amino acid residues, for example about 100 to 1000 amino acid residues, can be used as the foreign substance.

Typically, a suitable number for the total number of amino acid residues constituting the synthetic polypeptide prepared as the construct for transferring a foreign substance is several or several dozen (for example, 10) to 1000 or fewer, preferably 600 or fewer, and even more preferably 500 or fewer, and most preferably 300 or fewer (and further, 100 or fewer, e.g., 10 to 300). The polypeptide having such a length is easy to synthesize (biologically or chemically) and easy to use.

Preferably, the foreign substance to be used is a mature form or precursor (including pro-forms and prepro-forms) of a polypeptide involved in a function such as the development, differentiation, growth, malignant transformation, homeostasis, and regulation of metabolism in various cells and tissues (organs). Moreover, the present invention can be carried out to transfer a polypeptide with a heretofore unknown function into a cell to elucidate the function of the polypeptide with the cell (within a biological tissue).

For example, when the eukaryotic cell that is the target of transfer is a human or other mammalian stem cell (including somatic stem cells, embryonic stem cells, and induced pluripotent stem cells (hereinafter, iPS cells)), preferably the mature form or precursor of a peptide with various types of biological activity involving the induction of differentiation of the stem cell will be used. Moreover, when the eukaryotic cell that is the target of transfer is a cancer cell (tumor cell), preferably various polypeptides involved in the induction of apoptosis of the cancer cell (tumor cell) will be used.

Alternatively, in the past iPS cells have been prepared by transducing a plurality of genes (for example, Oct3/4, Sox2, Klf4, c-Myc, Nanog, Lin28) into a designated cell (for example, a human or other mammalian skin cell or other somatic cell), and at least one gene product (polypeptide) from among these genes can be transferred by the transfer method of the present invention in place of the technique. Thus, it will be possible to prepare iPS cells by transferring the products of the abovementioned genes (i.e., polypeptides) into the cells (preferably the nucleus) in place of the direct transduction of the genes.

Therefore, an example of one preferred embodiment of the present invention is a method for preparing iPS cells wherein the construct for transferring a foreign substance of the present invention is prepared using as the foreign substance a polypeptide (for example Sox2 protein), encoded by at least one of a plurality of genes (for example Sox2) involved in the preparation of iPS cells, and the construct is then transferred into a designated eucaryotic cell (such as a human dermal fibroblast, etc.)

Alternatively, for example, Patent Document 2 discloses partial amino acid sequences constituting the various SOCS (suppressor of cytokine signaling) proteins and other proteins of the same family (hereinafter, "SOCS proteins") that all have a SOCS-box, which is a region (amino acid sequence) that can bind to the elongin BC complex (specifically, a part of elongin C), which is known to form a complex with elongin A and act as a transcription regulating factor. Patent Document 2 also indicates that this amino acid sequence, which is contained in a specific region called the "BC-box" that is believed to bind with the elongin BC complex, has a high level of neurodifferentiation inducing activity in somatic stem cells.

Therefore, as one preferred mode of the present invention, a synthetic polypeptide to be transferred into a target eukaryotic cell (for example, a human or mammalian stem cell) can be prepared using any of the abovementioned SOCS proteins (see Non-Patent Document 2) as the polypeptide involved in inducing neurodifferentiation. Therefore, in accordance with the abovementioned explanation, the present invention provides a method for inducing the differentiation of at least one type of eukaryotic cell into a nerve cell. In other words, the present method includes synthesizing a peptide chain with an amino acid sequence consisting of an abovementioned SOCS protein or any other polypeptide involved in inducing neurodifferentiation on the N-terminal end or C-terminal end of the abovementioned carrier peptide fragment of the present invention, and supplying the synthetic polypeptide (i.e., the synthetic polypeptide that is the construct for transferring a foreign substance) to a test sample containing the target eukaryotic cell or tissue comprising the cell (typically, a culture containing the cell). Typically, this process further includes incubating the test sample to which the synthetic polypeptide has been supplied, i.e., maintaining the test sample under conditions enabling survival of the target cell for a predetermined time period (in other words, under conditions such that the construct for transferring a foreign substance can be transferred into the cells).

Furthermore, as in the case of the carrier peptide fragment of the present invention disclosed above, it is surely possible to also use, as polypeptide (foreign substance) involved in inducing neurodifferentiation, a modified amino acid sequence that is formed by the replacement, deletion, and/or addition (insertion) of one or several amino acid residues therein provided its function as a polypeptide related to inducing neurodifferentiation is retained.

The construct for transferring a foreign substance with the abovementioned configuration has a high level of neurodifferentiation-inducing activity toward at least one type of cell (typically a stem cell) as a neurodifferentiation-inducing polypeptide. Hence, it can most suitably be used as an active ingredient in a neurodifferentiation-inducing agent. It should be noted that the neurodifferentiation-inducing polypeptide contained in the neurodifferentiation-inducing agent can also take the form of a salt provided the neurodifferentiation-inducing activity thereof is not lost. For example, an acid addition salt of the polypeptide that is obtained by carrying out an addition reaction with a conventionally used inorganic or organic acid by conventional means can be used therefor. Alternatively, a different salt (for example, a metal salt) can be used provided it has neurodifferentiation-inducing activity.

The neurodifferentiation-inducing agent can contain a neurodifferentiation-inducing polypeptide of the abovementioned constitution as the active ingredient, as well as various medically (pharmaceutically) permissible carriers in accordance with the form of use. A carrier generally used in peptide medicines is preferably used as a diluent, excipient, and the like. The carrier will differ appropriately in accordance with the usage and form of the neurodifferentiation-inducing agent, but typical examples include water, a physiological buffer solution, and various organic solvents. The carrier can be an aqueous solution of alcohol (ethanol, etc.) at a suitable concentration, glycerol, or a non-drying oil such as olive oil. Alternatively, the carrier can be a liposome. Examples of a secondary ingredients that can be contained in the neurodifferentiation-inducing agent include various fillers, expanders, binders, moisturizers, surfactants, pigments, fragrances, etc.

The form of the neurodifferentiation-inducing agent is not particularly limited herein. Examples of typical forms include liquids, suspensions, emulsions, aerosols, foams, granules, powders, tablets, capsules, and ointments. Moreover, the agent can also be made into a lyophilized product or granulated product to be dissolved in physiological saline or a suitable buffer (e.g., PBS), etc., immediately before use and prepared as a liquid for injection, etc.

It should also be noted that prior art, publicly known methods can be used for the processes themselves whereby the neurodifferentiation-inducing polypeptide (main ingredient) and various carriers (secondary ingredients) are made into a material and then prepared as the medicines (compositions) in various forms, and a detailed explanation of the production process for drug product formulation itself is omitted herein because it is not a characterizing feature of the present invention. For example, *Comprehensive Medicinal Chemistry*, edited by Corwin Hansch, Pergamon Press, 1990, can be noted as a source of detailed information concerning formulations.

Exactly the desired amount of the neurodifferentiation-inducing agent provided by the present invention can be administered as a liquid medicine to a patient (i.e., to the body) by intravenous, intramuscular, subdermal, intradermal, or intraperitoneal injection. Alternatively, it can be administered orally in solid form such as a tablet, etc. Thus, typically neurons can be generated (produced) in vivo from somatic stem cells present at or near the diseased area. As a result, nerve regeneration can serve as a powerful therapeutic method that can effectively treat a variety of neurological disorders. For example, treatment of neurological disorders such as Parkinson's disease, cerebral infarction, Alzheimer's disease, paralysis of the body caused by trauma to the spinal cord, cerebral contusion, amyotrophic lateral sclerosis, Huntington's disease, brain tumor, retinal degeneration, and the like can be treated with a regenerative medicine approach.

Alternatively, by supplying a suitable amount of neurodifferentiation-inducing agent (neurodifferentiation-inducing polypeptide) to cellular material that has been temporarily or permanently resected from the body, i.e., living tissue or cell clusters (for example, a culture product of somatic stem cells), a target polypeptide can be transferred efficiently from outside the cells into the cytoplasm (more preferably, the nucleus) thereof, and neurons can be efficiently generated thereby. This means that large amounts of the desired neurons can be produced in the cellular material. Furthermore, by returning the neurons that were produced in large amounts or cellular material (living tissues and cell clusters) containing the produced neurons once again to the body (typically a diseased area requiring nerve regeneration), the same therapeutic efficacy can be obtained as when the neurodifferentiation-inducing agent (neurodifferentiation-inducing polypeptide) is administered directly to the body.

It is clear from the above explanation that, in a different aspect, the present invention can provide cells, cell clusters, and living tissues that are useful for treating neurological disorders and wherein differentiation to neurons has been induced by transferring the neurodifferentiation-inducing polypeptides into the cells.

Moreover, a polynucleotide coding for the neurodifferentiation-inducing polypeptide of the present invention can be used as a material for so-called gene therapy. For example, the neurodifferentiation-inducing polypeptide of the present invention can be expressed constantly in the body (cells) by incorporating a gene (typically a DNA segment or RNA segment) coding for the neurodifferentiation-inducing polypeptide into a suitable vector, and transfecting a target site therewith. Therefore, a polynucleotide (DNA segment, RNA segment, etc.) coding for the neurodifferentiation-inducing polypeptide of the present invention is useful as a drug for the prevention or treatment of a neurological disease in the abovementioned patients, etc.

At least one amino acid residue can be amidated in the construct for transferring a foreign substance (i.e., an artificially synthesized polypeptide) wherein the foreign substance is a polypeptide provided by the present invention such as the abovementioned neurodifferentiation-inducing polypeptide that is presented as a typical example. The structural stability (protease resistance) of the polypeptide in the cytoplasm and nucleus can be increased by amidation of the carboxyl group of an amino acid residue (typically the C-terminal amino acid residue of a polypeptide chain).

It is desirable for the total number of amino acid residues in the polypeptide chain constituting the artificial polypeptide to be several (for example, 10) or more and about 1000 or fewer (preferably, 600 or fewer, and particularly preferably 300 or fewer, e.g., 50 to 300, or 50 or fewer). Such a polypeptide having such a chain length can be easily configured by synthesis methods, and therefore can be easily supplied to a test sample containing the target eukaryotic cells.

It should also be noted that the conformation (three-dimensional structure) of the polypeptide is not particularly limited, but preferably it is a straight chain or helix from the standpoint of its not easily becoming an immunogen (antigen).

It should also be noted that as an artificial polypeptide preferably all of the amino acid residues are L-amino acids, but provided the desired function inherent in the carrier polypeptide fragment and polypeptide motif is not lost, part or all of the amino acid residues can be replaced by D-amino acids.

Moreover, an additional sequence that normally cannot occur in these sequences can be partly included therein provided the desired function inherent in the carrier peptide fragment and polypeptide serving as the foreign substance is not lost. For example, an amino acid sequence can be configured with a structure wherein several amino acid residues functioning as a linker (for example, glycine residues) can be positioned between the carrier peptide fragment and the foreign peptide motif.

Among artificial polypeptides (constructs for transferring a foreign substance) to be used, those with a relatively short peptide chain can easily be produced by conventional chemical synthesis methods. For example, a either prior art publicly known solid phase or liquid phase synthesis method can be used. Solid phase synthesis using Boc (t-butyloxycarbonyl) or Fmoc (9-fluoroenylmethoxycarbonyl) as an amine protecting group is preferred. In other words, a peptide chain with the desired amino acid sequence and modifications (C-terminal amidation, etc.) can be synthesized by solid phase synthesis using a commercially available peptide synthesizer (e.g., one obtainable from PerSeptive Biosystems, Applied Biosystems, etc.)

Alternatively, the artificial polypeptide (construct for transferring a foreign substance) can be synthesized using genetic engineering methods. This approach is preferred for producing a polypeptide with a relatively long peptide chain. In other words, a DNA nucleotide sequence (including the ATG start codon) that codes for the amino acid sequence of the desired artificial peptide is synthesized. Then a recombinant vector suitable for a host cell is configured with a genetic construct for expression that comprises the DNA and various regulatory elements (including a promoter, ribosome binding site, terminator, enhancer, and a cis-element for controlling the level of expression) to express the amino acid sequence in the host cell.

Using conventional techniques this recombinant vector is transferred to designated host cells (for example, yeast cells, insect cells, plant cells, or animal (mammal) cells), and the host cells, or an individual or tissue containing the cells is cultured under designated conditions. The target polypeptide can be expressed and produced in the cells thereby. Furthermore, a polypeptide comprising the target amino acid sequence can be obtained by isolating and purifying the polypeptide from the host cells (or from the culture medium if it is secreted). Using conventional techniques this recombinant vector is transferred to a designated host cell (for example, yeast, insect cell, plant cell, or mammalian cell), and the host cell, or an individual or tissue containing the cells is cultured under prescribed conditions. The target polypeptide can be expressed and produced in the cells thereby. Then the target peptide (i.e., construct for transferring a foreign substance) can be obtained by isolating and purifying the polypeptide from the host cells (or from the culture medium if it is secreted).

It should be noted that the method for configuring the recombinant vector and the method for transferring the configured recombinant vector to a host cell, etc., can utilize methods conventionally used in the fields without modification, and because those methods themselves are not a characterizing feature of the present invention, the detailed explanation thereof is omitted herein.

For example, a fusion protein expression system can be used for efficient, large volume production in host cells. More specifically, first the gene (DNA) coding for the amino acid sequence of the target polypeptide is prepared by chemical synthesis, and the synthesized gene is inserted at a suitable site in a suitable fusion protein expression vector (for example, a GST (glutathione S-transferase) fusion protein expression vector such as the pET series provided by Novagen and the pGEX series provided by Amersham Biosciences). Then the host cells (typically *E. coli*) are transformed by the vector. The resulting transformant is cultured to prepare the target fusion protein. Next the protein is extracted and purified. Then the resulting purified is cleaved by a designated enzyme (protease) and the freed target peptide fragment (i.e., the designed artificial polypeptide) is recovered by a method such as affinity chromatography. The target construct for transferring a foreign substance (artificial polypeptide) can be produced using this kind of prior art and publicly known fusion protein expression system (for example, the GST/His system provided by Amersham Biosciences can be utilized).

Alternatively, template DNA for use in a cell-free protein synthesis system (i.e., a synthetic gene fragment containing a nucleotide sequence coding for the amino acid sequence of the target artificial peptide) can be prepared, and in vitro synthesis of the target polypeptide can be carried out by employing a so-called cell-free protein synthesis system using the various compounds necessary for polypeptide synthesis (ATP, RNA polymerase, amino acids, etc.). References concerning a cell-free protein synthesis system include the papers by Shimizu et al. (Shimizu et al., Nature Biotechnology, 19, 751-755 (2001)), and Madin et al. (Madin et al., Proc. Natl. Acad. Sci. USA, 97(2), 559-564 (2000)). When the present application was filed there were already many companies carrying out polypeptide production on consignment based on the technology disclosed in these documents, and cell-free protein synthesis kits were commercially available (for example the wheat germ cell-free protein synthesis kit PROTEIOS® obtainable from Toyobo Co., Ltd., in Japan).

Therefore, if an amino acid sequence corresponding to the polypeptide that is the object of transfer into the cytoplasm (preferably, the nucleus) can be determined, and a peptide chain can be designed that combines the same with the cell membrane-permeating carrier peptide fragment represented by abovementioned SEQ ID NO: 1, the intended artificial polypeptide can easily be synthesized and produced by a cell-free protein synthesis system based on its amino acid sequence. For example, the polypeptide can easily be produced with the PURESYSTEM® from Japan's Post Genome Institute Co., Ltd. Several examples concerning the present invention are described below, but the present invention is by no means limited to the items presented in these examples.

Example 1

Preparation of Construct for Transferring a Foreign Substance

A total of two types (Sample Nos. 1 and 2) of constructs for transferring a foreign substance were produced that had a relatively high molecular weight polypeptide of 100 or more amino acid residues as the foreign substance.

In other words, as the foreign polypeptide Sample No. 1 used the SOX2 protein (i.e., a transcription factor providing an HMG domain with DNA binding capability and a transcription activation domain, hereinafter, "SOX2") which is a product of Sox2, a gene that is used for preparing the abovementioned iPS cells.

Moreover, as the foreign polypeptide Sample No. 2 used the fluorescent protein GFP (Green Fluorescent Protein).

It should be noted that the amino acid sequence of SOX2 (317 amino acid residues) is represented by SEQ ID NO: 2, and the amino acid sequence of GFP (238 amino acid residues) is represented by SEQ ID NO: 3.

In other words, a fusion gene (artificially synthesized DNA) was prepared to code for a polypeptide containing an NoLS fused onto the N-terminal end of a foreign polypeptide (i.e., SOX2 or GFP). Furthermore, a single methionine residue, which is a start code, was added to the N-terminal end of the NoLS. Moreover, a polyhistidine region was formed on the C-terminal end of the foreign polypeptide for purification by the histidine trap column described below.

Here the detailed nucleotide sequences of the designed and synthesized fusion genes and the amino acid sequences encoded thereby are shown as SEQ ID Nos.: 4 and 5 for Sample No. 1 (nols-sox2) and as SEQ ID NOS: 6 and 7 for Sample No. 2 (nlos-gfp).

The target fusion polypeptides (Sample No. 1 and Sample No. 2) were biosynthesized using these synthetic genes by a baculovirus expression system using conventional insect cells.

Both ends of the abovementioned synthetic DNA (gene) molecules were cleaved by the restriction enzymes Bgl-II and Xba-I (both a product of Takara Bio Inc.), and were incorporated into a pM15 vector cleaved with the same restriction enzymes (Katakura Industries Co., Ltd.) to prepare transfer vectors.

Next BmN cells (Katakura Industries Co., Ltd.) were co-transfected with the transfer vectors prepared in the above-mentioned manner and the genomic DNA of a baculovirus CPd strain (Katakura Industries Co., Ltd.) to prepare a recombinant virus.

The resulting recombinant viruses were used to infect 5 silkworms (*Bombyx mori*, Katakura Industries Co., Ltd.). The infected silkworms were raised until they formed chrysalises, and then the chrysalises were placed in homogenization buffer (comprising 20 mM Tris-HCl (pH 8.0), 150 mM NaCl, 1 mM EDTA, 1 mM EGTA, 10% glycerol, 10 mM benzamidine, 1 mM PMSF, and 1 mM DTT) and homogenized using a homogenizer with a Teflon® tip. A surfactant (brand name: Tween 20) was added to the resulting silkworm homogenate to a concentration of 1%, solubilization was performed by stirring for 1 hour at 4° C., and ultracentrifugation (100,000 g×1 hour) was performed to separate the supernatant (soluble fraction) from the precipitate (insoluble fraction).

To find the production region for Sample No. 1, a Western blot analysis was then carried out using an anti-SOX2 antibody (murine monoclonal antibody product of ABGENT). Results confirmed that the NoLS-SOX2 fusion protein (hereinafter, Sample No. 1 polypeptide) was present in the insoluble fraction.

Then the insoluble fraction was suspended in a phosphate buffer (pH 7.5, containing 0.5 M NaCl, 1 mM DTT, 5 mM imidazole, and 8 M urea) as a solubilization buffer, and the fraction was solubilized by stirring for 1 hour at room temperature.

As noted above, a polyhistidine sequence (His tag) was added to the C-terminal end of the resulting fusion polypeptide, and purification (concentration) of the fusion polypeptide was carried out by utilizing this sequence. Specifically, the abovementioned solubilized polypeptide solution was added to a commercially available histidine trap (H isTrap) column (product of GE Healthcare), and the polypeptide of Sample No. 1 was adsorbed onto the column. Next, the column was rinsed well with solubilization buffer, and then the buffer was replaced with refolding buffer (phosphate buffer (pH 7.5) containing 0.5 M NaCl, 1 mM DTT, and 5 mM imidazole), and the polypeptide was refolded in the column.

Then the column was rinsed well with the buffer, and the protein was eluted with elution buffer (phosphate buffer (pH 7.5) containing 0.5 M NaCl and 0.5 M imidazole). Thus, a solution containing the purified Sample No. 1 polypeptide was obtained.

To find the production area of Sample No. 2, a Western blot analysis was then carried out using an anti-GFP antibody (rabbit polyclonal antibody, product of Invitrogen). From the results it was learned that the NoLS-GFP fusion protein (hereinafter, Sample No. 2 polypeptide) was present in the soluble fraction. The buffer was replaced with refolding buffer using a PD-10 desalting column (product of GE Healthcare), the solution was added to the abovementioned H isTrap column, and the Sample No. 2 polypeptide was adsorbed onto the column. Next, the column was rinsed well with the same buffer, and the bound protein was eluted using the elution buffer. Thus, a solution containing the purified Sample No. 2 polypeptide was obtained.

After the buffer for the resulting two types of purified polypeptides was replaced with DulBecco phosphate buffer (Wako Pure Chemical Industries, hereinafter "D-PBS") using a PD-10 desalting column, the solutions were sterilized by filtration using a 0.45 μm filter, and used in the following tests.

Example 2

Evaluation of Cell Membrane Permeability Function of Sample No. 1 and Sample No. 2

Human neonate fibroblasts (ATCC cell line CCD-1079sk) were used as the eukaryotic cells, and the cell membrane permeability capability of the 2 samples (constructs for transferring a foreign substance) obtained in Example 1 above was investigated.

More specifically, approximately $2 \times 10^4$ cells were cultured on a collagen-coated S-well slide overnight at 37° C. in 5% $CO_2$ using a liquid culture medium (Eagle's MEM medium: comprising 0.1 mM NeAA, 1 mM sodium pyruvate, Earle's BSS (product of GIBCO) with 10% FBS (product of GIBCO).

The purified polypeptides obtained above were added to the cell culture (1.5 μg/mL of the polypeptide of Sample No. 1 and 3.5 μg/mL of the polypeptide of Sample No. 2), and culturing was continued for another 2 hours.

Then the supernatant was removed, the abovementioned D-PBS was added, and the cells were rinsed 3 times therewith on ice. Next, ice-cold methanol was added and the samples were let stand for 10 min at −20° C. to fix the cells. Then the methanol was removed, PBS solution containing 5% normal goat serum (product of MBL) was added, and blocking was carried out at room temperature for 1 hour. After the blocking solution was removed and the cells were rinsed once with PBS, anti-SOX2 antibody diluted 200-fold in PBS was added to the wells to which the polypeptide of Sample No. 1 had been added and to the control wells (to which only PBS had been added), and the slides were let stand for 1 hour at room temperature. Meanwhile, anti-GFP antibody diluted 500-fold in PBS was added to the wells to which the polypeptide of Sample No. 2 had been added, and the slides were let stand for 1 hour at room temperature.

After the time period for the antigen-antibody reaction had elapsed, the solutions were removed from the wells, the cells were rinsed 3 times with PBS, anti-mouse IgG antibody-fluorescent dye (Alexa 555) labeling agent (product of Invitrogen) diluted 800-fold in PBS was added to the wells to which the anti-SOX2 antibody had been added, and the cells were let stand for 1 hour at room temperature. Meanwhile, anti-rabbit IgG antibody-fluorescent dye (Alexa 555) labeling agent (product of Invitrogen) diluted 800-fold in PBS was added to the wells to which the anti-GFP antibody had been added, and the cells were let stand for 1 hour at room temperature.

Thereafter, the solution was removed, the cells were rinsed 3 times in PBS, sealed with a cover glass and a DAPI-containing mounting medium (product of Invitrogen), and the fluorescence was observed with a confocal laser scanning microscope.

FIG. 1 shows the results of the test area to which the polypeptide of Sample No. 1 (NoLS-SOX2) was added, and FIG. 2 shows the results of the test area to which the polypeptide of Sample No. 2 (NoLS-GFP) was added.

As can clearly be seen from FIG. 1 (micrograph), in the cells to which the polypeptide was not added, only nuclear staining by DAPI can be seen, and staining by the anti-SOX2 antibody cannot be seen at all. However, transfer of the polypeptide into the cells can be seen in the cells from the culture liquid to which the polypeptide of Sample No. 1 was added. Furthermore, judging from the location of the stain, it was confirmed that the polypeptide transferred into the cells was transferred (translocated) to the nucleus and localized therein. This finding demonstrates that the carrier peptide fragment of the present invention contained in the polypeptide of Sample No. 1 can transfer the SOX2 polypeptide comprising 300 or more amino acid residues into the cytoplasm from outside the cell, and further into the nucleus.

Similarly, as can clearly be seen from FIG. 2 (micrograph), in the cells to which the polypeptide was not added, only nuclear staining by DAPI can be seen, and staining by the anti-GFP antibody cannot be seen at all. However, transfer of the polypeptide into the cells can be seen in the cells from the culture liquid to which the polypeptide of Sample No. 2 was added. Furthermore, judging from the location of the stain, it was confirmed that the polypeptide transferred into the cells was transferred (translocated) to the nucleus and localized therein. This finding demonstrates that the carrier peptide fragment of the present invention contained in the polypeptide of Sample No. 2 can transfer the GFP polypeptide, which is 200 or more amino acid residues, into the cytoplasm from outside the cell, and further into the nucleus.

The above examples clearly show that as a particularly preferred mode of the method for transferring a foreign substance disclosed herein, the present invention provides a method for transferring a foreign substance of interest from outside a human or nonhuman mammalian cell into the cytoplasm of the cell (more preferably into the nucleus as well) by using a carrier peptide fragment comprising the amino acid sequence of SEQ ID NO: 1 or a modified amino acid sequence formed by the substitution, deletion and/or addition (insertion) of 1, 2, or 3 amino acid residues in the amino acid sequence as the abovementioned carrier peptide fragment. The carrier peptide fragment comprising the amino acid sequence of SEQ ID NO: 1 can be most suitably used for transferring a polypeptide with a relatively large molecular weight (typically about 100 to 1000 (e.g., 200 to 600) amino acid residues) into a stem cell such as an iPS cell, ES cell, etc., or into another somatic cell. Specific examples of the present invention have been described in detail above, but these are merely exemplary and by no means limit the scope of the claims herein. The technology disclosed in the claims includes various changes to and variations of the specific examples presented above.

INDUSTRIAL APPLICABILITY

The present invention enables the transfer of a foreign substance of interest having a designated function into a human or other mammalian cell (for example, skin cell, nerve cell or other somatic cell, somatic stem cell, induced pluripotent stem cell and ES cell). Thereby it is possible to transform the target cell in accordance with the foreign substance (polypeptide, etc.) to be transferred, and for example, bring about the differentiation thereof to a specific cell type (nerve cell, bone cell, muscle cell, skin cell, etc.)

The present invention provides an artificially prepared construct for transferring a foreign substance of interest from outside a eukaryotic cell (in particular, various animal cells typified by human and nonhuman mammalian cells that do not have a cell wall) at least into the cytoplasm (preferably, into the nucleus as well) thereof. By utilizing this construct, a foreign substance of interest can be effectively transferred into a target cell, and cells wherein the foreign substance has been transferred, as well as organs and other body tissues comprising cells that contain the foreign substance can be obtained thereby.

SEQUENCE LISTING FREE TEXT

Synthetic peptide of SEQ ID NO: 1
Synthetic substance of SEQ ID NO: 4
Synthetic substance of SEQ ID NO: 5
Synthetic substance of SEQ ID NO: 6
Synthetic substance of SEQ ID NO: 7

The invention claimed is:

1. A method for transferring a foreign substance of interest from outside a eukaryotic cell at least into the cytoplasm of the cell, comprising the steps of:
    (a) preparing a construct comprising:
        a carrier peptide fragment consisting of the amino acid sequence of SEQ ID NO: 1; and
        a foreign substance of interest bonding directly or indirectly via a linker to the N-terminus and/or C-terminus of the carrier peptide fragment;
    (b) adding the construct containing the carrier peptide fragment to a culture medium that includes the eukaryotic cell or a tissue containing the cell;
    (c) culturing the eukaryotic cell or the tissue containing the cell in the medium containing the construct; and
    (d) transferring the construct into the culturing eukaryotic cell from outside of the cell by cell membrane permeability of the carrier peptide fragment itself.

2. The method according to claim 1, wherein the foreign substance is any organic compound selected from the group consisting of peptides, nucleic acids, dyes, and drugs.

3. The method according to claim 2, wherein the foreign substance is a mature polypeptide originating in any biological species, or a precursor polypeptide thereof, and the construct for transferring a foreign substance is a synthetic polypeptide comprising an amino acid sequence corresponding to the mature polypeptide or precursor polypeptide thereof as the foreign substance, and the amino acid sequence of the carrier peptide fragment.

4. The method according to claim 3, wherein the mature polypeptide or precursor polypeptide thereof used as the foreign substance comprises between 100 and 1000 amino acid residues.

5. The method according to claim 1, wherein the eukaryotic cell that is the target to which the construct for transferring a foreign substance is to be transferred is a human or nonhuman mammalian cell.

\* \* \* \* \*

```
                        SEQUENCE LISTING

<160> NUMBER OF SEQ ID NOS: 7

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Lys Lys Arg Thr Leu Arg Lys Asn Asp Arg Lys Lys Arg
1               5                   10

<210> SEQ ID NO 2
<211> LENGTH: 317
<212> TYPE: PRT
<213> ORGANISM: Homo sapiens

<400> SEQUENCE: 2

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
                20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
        50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110
```

```
Arg Arg Lys Thr Lys Thr Leu Met Lys Asp Lys Tyr Thr Leu Pro
            115                 120                 125
Gly Gly Leu Leu Ala Pro Gly Gly Asn Ser Met Ala Ser Gly Val Gly
130                 135                 140
Val Gly Ala Gly Leu Gly Ala Gly Val Asn Gln Arg Met Asp Ser Tyr
145                 150                 155                 160
Ala His Met Asn Gly Trp Ser Asn Gly Ser Tyr Ser Met Met Gln Asp
                165                 170                 175
Gln Leu Gly Tyr Pro Gln His Pro Gly Leu Asn Ala His Gly Ala Ala
                180                 185                 190
Gln Met Gln Pro Met His Arg Tyr Asp Val Ser Ala Leu Gln Tyr Asn
            195                 200                 205
Ser Met Thr Ser Ser Gln Thr Tyr Met Asn Gly Ser Pro Thr Tyr Ser
    210                 215                 220
Met Ser Tyr Ser Gln Gln Gly Thr Pro Gly Met Ala Leu Gly Ser Met
225                 230                 235                 240
Gly Ser Val Val Lys Ser Glu Ala Ser Ser Ser Pro Pro Val Val Thr
                245                 250                 255
Ser Ser His Ser Arg Ala Pro Cys Gln Ala Gly Asp Leu Arg Asp
                260                 265                 270
Met Ile Ser Met Tyr Leu Pro Gly Ala Glu Val Pro Glu Pro Ala Ala
            275                 280                 285
Pro Ser Arg Leu His Met Ser Gln His Tyr Gln Ser Gly Pro Val Pro
    290                 295                 300
Gly Thr Ala Ile Asn Gly Thr Leu Pro Leu Ser His Met
305                 310                 315

<210> SEQ ID NO 3
<211> LENGTH: 238
<212> TYPE: PRT
<213> ORGANISM: Aequorea victoria

<400> SEQUENCE: 3

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
                20                  25                  30
Gly Glu Gly Asp Ala Thr Tyr Gly Lys Leu Thr Leu Lys Phe Ile Cys
            35                  40                  45
Thr Thr Gly Lys Leu Pro Val Pro Trp Pro Thr Leu Val Thr Thr Phe
50                  55                  60
Gly Tyr Gly Val Gln Cys Phe Ala Arg Tyr Pro Asp His Met Lys Gln
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
```

```
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 4
<211> LENGTH: 8773
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (8)..(1078)
<223> OTHER INFORMATION:

<400> SEQUENCE: 4
```

| | | | | | | | | | | | | | | | | |
|---|---|---|---|---|---|---|---|---|---|---|---|---|---|---|---|---|
| agatctt | atg | aag | aaa | cgc | acc | ttg | cgc | aag | aac | gac | cgc | aag | aag | cgc | | 49 |
| | Met | Lys | Lys | Arg | Thr | Leu | Arg | Lys | Asn | Asp | Arg | Lys | Lys | Arg | | |
| | 1 | | | 5 | | | | | 10 | | | | | | | |
| atg | tac | aac | atg | atg | gag | acg | gag | ctg | aag | ccg | ccg | ggc | ccg | cag | caa | 97 |
| Met | Tyr | Asn | Met | Met | Glu | Thr | Glu | Leu | Lys | Pro | Pro | Gly | Pro | Gln | Gln |  |
| 15 | | | | | 20 | | | | | 25 | | | | | 30 | |
| act | tcg | ggg | ggc | ggc | ggc | ggc | aac | tcc | acc | gcg | gcg | gcg | gcc | ggc | ggc | 145 |
| Thr | Ser | Gly | Gly | Gly | Gly | Gly | Asn | Ser | Thr | Ala | Ala | Ala | Ala | Gly | Gly | |
| | | | | 35 | | | | | 40 | | | | | 45 | | |
| aac | cag | aaa | aac | agc | ccg | gac | cgc | gtc | aag | cgg | ccc | atg | aat | gcc | ttc | 193 |
| Asn | Gln | Lys | Asn | Ser | Pro | Asp | Arg | Val | Lys | Arg | Pro | Met | Asn | Ala | Phe | |
| | | | 50 | | | | | 55 | | | | | 60 | | | |
| atg | gtg | tgg | tcc | cgc | ggg | cag | cgg | cgc | aag | atg | gcc | cag | gag | aac | ccc | 241 |
| Met | Val | Trp | Ser | Arg | Gly | Gln | Arg | Arg | Lys | Met | Ala | Gln | Glu | Asn | Pro | |
| | | 65 | | | | | 70 | | | | | 75 | | | | |
| aag | atg | cac | aac | tcg | gag | atc | agc | aag | cgc | ctg | ggc | gcc | gag | tgg | aaa | 289 |
| Lys | Met | His | Asn | Ser | Glu | Ile | Ser | Lys | Arg | Leu | Gly | Ala | Glu | Trp | Lys | |
| 80 | | | | | 85 | | | | | 90 | | | | | | |
| ctt | ttg | tcg | gag | acg | gag | aag | cgg | ccg | ttc | atc | gac | gag | gct | aag | cgg | 337 |
| Leu | Leu | Ser | Glu | Thr | Glu | Lys | Arg | Pro | Phe | Ile | Asp | Glu | Ala | Lys | Arg | |
| 95 | | | | | 100 | | | | | 105 | | | | | 110 | |
| ctg | cga | gcg | ctg | cac | atg | aag | gag | cac | ccg | gat | tat | aaa | tac | cgg | ccc | 385 |
| Leu | Arg | Ala | Leu | His | Met | Lys | Glu | His | Pro | Asp | Tyr | Lys | Tyr | Arg | Pro | |
| | | | | 115 | | | | | 120 | | | | | 125 | | |
| cgg | cgg | aaa | acc | aag | acg | ctc | atg | aag | aag | gat | aag | tac | acg | ctg | ccc | 433 |
| Arg | Arg | Lys | Thr | Lys | Thr | Leu | Met | Lys | Lys | Asp | Lys | Tyr | Thr | Leu | Pro | |
| | | | 130 | | | | | 135 | | | | | 140 | | | |
| ggc | ggg | ctg | ctg | gcc | ccc | ggc | ggc | aat | agc | atg | gcg | agc | ggg | gtc | ggg | 481 |
| Gly | Gly | Leu | Leu | Ala | Pro | Gly | Gly | Asn | Ser | Met | Ala | Ser | Gly | Val | Gly | |
| | | | 145 | | | | | 150 | | | | | 155 | | | |
| gtg | ggc | gcc | ggc | ctg | ggc | gcg | ggc | gtg | aac | cag | cgc | atg | gac | agt | tac | 529 |
| Val | Gly | Ala | Gly | Leu | Gly | Ala | Gly | Val | Asn | Gln | Arg | Met | Asp | Ser | Tyr | |
| | 160 | | | | | 165 | | | | | 170 | | | | | |
| gcg | cac | atg | aac | ggc | tgg | agc | aac | ggc | agc | tac | agc | atg | atg | cag | gac | 577 |
| Ala | His | Met | Asn | Gly | Trp | Ser | Asn | Gly | Ser | Tyr | Ser | Met | Met | Gln | Asp | |
| 175 | | | | | 180 | | | | | 185 | | | | | 190 | |
| cag | ctg | ggc | tac | ccg | cag | cac | ccg | ggc | ctc | aat | gcg | cac | ggc | gca | gcg | 625 |
| Gln | Leu | Gly | Tyr | Pro | Gln | His | Pro | Gly | Leu | Asn | Ala | His | Gly | Ala | Ala | |
| | | | | 195 | | | | | 200 | | | | | 205 | | |
| cag | atg | cag | ccc | atg | cac | cgc | tac | gac | gtg | agc | gcc | ctg | cag | tac | aac | 673 |

```
                    -continued

Gln Met Gln Pro Met His Arg Tyr Asp Val Ser Ala Leu Gln Tyr Asn
                      210                 215                 220 tcc atg acc agc tcg cag acc tac atg aac ggc tcg ccc acc tac agc          721
Ser Met Thr Ser Ser Gln Thr Tyr Met Asn Gly Ser Pro Thr Tyr Ser
            225                 230                 235 atg tcc tac tcg cag cag ggc acc cct ggc atg gct ctt ggc tcc atg          769
Met Ser Tyr Ser Gln Gln Gly Thr Pro Gly Met Ala Leu Gly Ser Met
        240                 245                 250 ggt tcg gtg gtc aag tcc gag gcc agc tcc agc ccc cct gtg gtt acc          817
Gly Ser Val Val Lys Ser Glu Ala Ser Ser Ser Pro Pro Val Val Thr
255                 260                 265                 270 tct tcc tcc cac tcc agg gcg ccc tgc cag gcc ggg gac ctc cgg gac          865
Ser Ser Ser His Ser Arg Ala Pro Cys Gln Ala Gly Asp Leu Arg Asp
                275                 280                 285 atg atc agc atg tat ctc ccc ggc gcc gag gtg ccg gaa ccc gcc gcc          913
Met Ile Ser Met Tyr Leu Pro Gly Ala Glu Val Pro Glu Pro Ala Ala
            290                 295                 300 ccc agc aga ctt cac atg tcc cag cac tac cag agc ggc ccg gtg ccc          961
Pro Ser Arg Leu His Met Ser Gln His Tyr Gln Ser Gly Pro Val Pro
        305                 310                 315 ggc acg gcc att aac ggc aca ctg ccc ctc tca cac atg tct aga ctg         1009
Gly Thr Ala Ile Asn Gly Thr Leu Pro Leu Ser His Met Ser Arg Leu
320                 325                 330 gtt ccg cgt gga tcc ggc tct gga tct ggc ctc agg atg ggg ggt tct         1057
Val Pro Arg Gly Ser Gly Ser Gly Ser Gly Leu Arg Met Gly Gly Ser
335                 340                 345                 350 cat cat cat cat cat cat ggc tagatacgcg aacgccggca tcagtgcctg            1108
His His His His His His Gly
                    355 ggccaggcct aaaacacta tacattgtta ttagtacatt tattaagcgt tagattctgt        1168
gcgttgttga tttacagaca attgttgtac gtattttaat aattcattaa atttgtaatc      1228
tttagggtgg tatgttagag cgaaaatcaa atgattttca gcgtctttgt atctgaattt      1288
aaatattaaa tcctcaatag atttgtaaaa taggtttcga ttggtttcaa acaagggttg      1348
tttttgcaaa ccgatggctg gactatctaa tggattttcg ctcaacacca cacgacttgc      1408
caaatcttgt agcagcaatc tagctttgtc gatattcgtt tgtgttttgt tttgtaataa      1468
agattcgacg tcgttcaaaa tattatgcgc ttttgtattt ttttcatcac tgtcgttggt      1528
gtacaattga ctcgacgtaa acacgttaaa taaagcttgg acatatttaa catcgggcgc      1588
gttaggccga ttattgccgc cgtcgtccca accctcgtcg ttagaagttg cttccgaaga      1648
cgattttgcc atagccacac gacgcctatt aattgtgtcg actaacacgt ccgcgatcaa      1708
atttttagtt gttgagtttt tcggaattat ttctgattgc ggacgttttt gtgcgggttt      1768
caatctaact gtgcccgatt taattcaga caacacgtta gaaagcgatg gtgcaggcgg       1828
tggtaacatt tcagccggca aatctactaa tggcggctgt aatggagctg atgataaatc      1888
tatcattggt ggaggcgcag gcggggctgg cggcggaggt ggtggcggcg tgatgcaga       1948
cggcggtttg ggctctttag caacacagt cgtcggcacc tcaattattg tattggtttc       2008
gggcgccgtt tttggtttga ccggtctgag acgagtgcga ttttttttcgt ttctaatagc    2068
ttccaacaat tgttgtctgt cgtctaaagg tgcagcgggt tgaggtttag tcggcattgg     2128
tggagcgggc gcaattcag acatcgatga tggcggtggt ggtggtggag gtggaggcgc      2188
tggaatgtta ggcacggaag aaggtggtgg cggtgccgcc ggtattataa tttgttctgg    2248
tttagtttgt tcgtgcacga ttgtgggcac cggcgcaggc gccgctggct gcacaacgga   2308
aggtcgtctg cttcgaggca gcgcttgggg tggtggcggc ggcaattcaa tattataatt   2368
```

```
ggaatacaaa tcgtaaaaat ctgctataag cattgtaatt tcgctatcgt ttaccgtgcc   2428
gatatttaac aatcgctcaa tgtaagcaat tgtattgtag agggattgtc tcaagctcgg   2488
atcccgcacg ttgatgacaa gccttttcat ttttaccaca gcattgtagt agcgagacac   2548
ttcgctgtcg tcgacgtaca tgtacgcttt gttgtcaaaa acgtcgttgg caaactttaa   2608
aatatttaaa aaaacatctc tgttcagcaa cactgtgttg tcgtaaatgc tgtctttgat   2668
aatttgcgct tccgcagtat cgacgcgttc aaaaaattga tgtgcatcaa ttttattgtt   2728
cctattattg aataaataag attgtacaga ttcatattta cgattcgtca tggccaccac   2788
caccgccaca aatgctacgc tgcaaacgct ggtacaattt tacgaaaact gcaaaaacgt   2848
caaaactcgg tataaaataa tcaacgggcg ttttggcaaa atatctattt tatcgcacaa   2908
gcccactagc aaattgtatt tgcagaaaac aatttcggcg cacaatttta acgtcgacga   2968
aataaaagtc caccagttaa tgaacgacca cccaaatttt ataaaaatct attttaatca   3028
cggtttcatt aacaaccaag tgatcgtgat ggactacatc gactgtccgg atttatttga   3088
aacgctacaa attaaaggcg agctttcgca ccaacttgtt agcaatatta ttagacaact   3148
gtgtgaagcg ctcaacgatt tgcacaaaca caatttcata cacaacgaca taaaactcga   3208
aaatgtctta tatttcgaag cactcgatcg cgtgtatgtt tgcgattacg gattgtgcaa   3268
acacgaaaac ttacccagcg tgcacgacgg cacgttggag tattttagtc cggaaaaaat   3328
tcgacgccac aactatgcac gttcgtttga ctggtacgcc gtcggcgtgt aacgtacaa   3388 gttgctaacc ggcggccgac acccgtttga aaaaagcgaa gacgaaatgt tggacttgaa   3448
tagcatgaag cgtcgtcagc aatacaacga cattggtgtt ttaaaacacg ttcgtaacgt   3508
taacgctcgt gactttgtgt actgcctaac aagatacaac ctagattgta gactaacaaa   3568
ttacaaacaa attataaaac atgagttttt gtcgtgagtg gtgttaataa aaatcataaa   3628
aattattgta aatgttttatt atttaaaaac gattcaaata tataataaaa acaatctaca   3688
tctatttctt cacaatccat aacacacaac aggtccatca atgagttttt gtctttatct   3748
gacatactat gtgcatgtaa caaatcaaat acatctttta aatctctata cacatctata   3808
cattgtctac caaaatcttt aataactgta taacatgaaa aagacttttc ttcttgcgtg   3868
gttttgccgc gtagatattg aaataaaatg tgcatgcaag cttggcactg gccgtcgttt   3928
tacaacgtcg tgactgggaa aaccctggcg ttacccaact taatcgcctt gcagcacatc   3988 ccccttcgc cagctggcgt aatagcgaag aggcccgcac cgatcgccct tcccaacagt   4048
tgcgcagcct gaatggcgaa tggaaattgt aagcgttaat attttgttaa aattcgcgtt   4108 aaattttgt taaatcagct cattttttaa ccaataggcc gaaatcggca aaatccctta   4168
taaatcaaaa gaatagaccg agatagggtt gagtgttgtt ccagtttgga acaagagtcc   4228
actattaaag aacgtggact ccaacgtcaa agggcgaaaa accgtctatc agggcgatgg   4288
cccactacgt gaaccatcac cctaatcaag ttttttgggg tcgaggtgcc gtaaagcact   4348
aaatcggaac cctaaaggga gcccccgatt tagagcttga cggggaaagc cggcgaacgt   4408
ggcgagaaag gaagggaaga aagcgaaagg agcgggcgct agggcgctgg caagtgtagc   4468
ggtcacgctg cgcgtaacca ccacacccgc cgcgcttaat gcgccgctac agggcgcgtc   4528
aggtggcact tttcggggaa atgtgcgcgg aaccccctatt tgtttatttt tctaaataca   4588
ttcaaatatg tatccgctca tgagacaata accctgataa atgcttcaat aatattgaaa   4648
aaggaagagt atgagtattc aacatttccg tgtcgccctt attccctttt ttgcggcatt   4708
ttgccttcct gttttttgctc acccagaaac gctggtgaaa gtaaaagatg ctgaagatca   4768
```

```
gttgggtgca cgagtgggtt acatcgaact ggatctcaac agcggtaaga tccttgagag    4828
ttttcgcccc gaagaacgtt ttccaatgat gagcactttt aaagttctgc tatgtggcgc    4888
ggtattatcc cgtattgacg ccgggcaaga gcaactcggt cgccgcatac actattctca    4948
gaatgacttg gttgagtact caccagtcac agaaaagcat cttacggatg gcatgacagt    5008
aagagaatta tgcagtgctg ccataaccat gagtgataac actgcggcca acttacttct    5068
gacaacgatc ggaggaccga aggagctaac cgcttttttg cacaacatgg gggatcatgt    5128
aactcgcctt gatcgttggg aaccggagct gaatgaagcc ataccaaacg acgagcgtga    5188
caccacgatg cctgtagcaa tggcaacaac gttgcgcaaa ctattaactg gcgaactact    5248
tactctagct tcccggcaac aattaataga ctggatggag gcggataaag ttgcaggacc    5308
acttctgcgc tcggcccttc cggctggctg gtttattgct gataaatctg gagccggtga    5368
gcgtgggtct cgcggtatca ttgcagcact ggggccagat ggtaagccct cccgtatcgt    5428
agttatctac acgacgggga gtcaggcaac tatgatgaa cgaaatagac agatcgctga    5488
gataggtgcc tcactgatta agcattggta actgtcagac caagtttact catatatact    5548
ttagattgat ttaaaacttc attttaatt taaaaggatc taggtgaaga tcctttttga    5608
taatctcatg accaaaatcc cttaacgtga gttttcgttc cactgagcgt cagacccgt    5668
agaaaagatc aaaggatctt cttgagatcc ttttttttctg cgcgtaatct gctgcttgca    5728
aacaaaaaaa ccaccgctac cagcggtggt ttgtttgccg gatcaagagc taccaactct    5788
ttttccgaag gtaactggct tcagcagagc gcagatacca atactgttc ttctagtgta    5848
gccgtagtta ggccaccact tcaagaactc tgtagcaccg cctacatacc tcgctctgct    5908
aatcctgtta ccagtggctg ctgccagtgg cgataagtcg tgtcttaccg ggttggactc    5968
aagacgatag ttaccggata aggcgcagcg gtcgggctga acggggggtt cgtgcacaca    6028
gcccagcttg gagcgaacga cctacaccga actgagatac ctacagcgtg agctatgaga    6088
aagcgccacg cttcccgaag ggagaaaggc ggacaggtat ccggtaagcg cagggtcgg    6148
aacaggagag cgcacgaggg agcttccagg gggaaacgcc tggtatcttt atagtcctgt    6208
cgggtttcgc cacctctgac ttgagcgtcg atttttgtga tgctcgtcag ggggcggag    6268
cctatggaaa aacgccagca acgcggcctt tttacggttc ctggccttt gctggccttt    6328
tgctcacatg ttctttcctg cgttatcccc tgattctgtg ataaccgta ttaccgcctt    6388
tgagtgagct gataccgctc gccgcagccg aacgaccgag cgcagcgagt cagtgagcga    6448
ggaagcggaa gagcgcccaa tacgcaaacc gcctctcccc gcgcgttggc cgattcatta    6508
atgcagctgg cacgacaggt ttcccgactg gaaagcgggc agtgagcgca acgcaattaa    6568
tgtgagttag ctcactcatt aggcaccca ggctggccgc aattcagaga aaccagtcgc    6628
cgcgtcaagt ttgtagtctg gccgatcttg aacagattcc tttcggcgta cagcagcgtc    6688
gtggccgcat agaaatggcc ctcgacggga gcggaattaa actttactgt cgcttgggcg    6748
tcttggagca ggctcaacgc cgactgtcgg gcggtgcact ggggcaacac gtgttcgtaa    6808
aaccaatttt gcagctccgc cgcgttggtc atcttggagc gcatgaacaa ctgtataacg    6868
cctattttgt cgagtaatat tgtttgcgtc tgcaaataca gcggattgcc ttgtttaacg    6928
tgttttcttt tgctgatatt aatacacgct tgctcgaatg tgcatttgta cttgccgtcg    6988
acgtgatctc taattgcttt tttggtgttt ttaaattta atttgtttgc aatgtccctg    7048
gccacaaatc tgaccggctg ctcgccgccg agcacgtacc tcagcgtgaa cgtgtcttca    7108
ccgaatttga acttgccaat tttaacttga gccatttttt atttacaaac tacgcgtaga    7168
```

-continued

```
gattcgacga aagcgcaaaa caaactgaga acaactagta gtggtgttgc tacaaattcc      7228
ctccggcgtt gatgcgctgc acttcaaata gttcgttgac gccctcctcc gtttcgccaa      7288
acacgtccaa cgggtggtcg ataaccagca gcgtgccgca cgcaacgcac aagtatctgt      7348
acaccgaatg atcgtcgggc gaaggcacgt cggcctccaa gtggcaatat tggcaaattc      7408
gaaaatatat acaattgggt tgtttgcgca tatctatcgt ggcgttgggc atgtacgtct      7468
gaacgttgat ttgcatgcaa gccgaaatta aatcattgcg attaatgcga ttaaaacgtt      7528
gtacatcctc gtttttaatc atgccgtcga ttagatcgcg caatcgagtc aagtggtcaa      7588
agtgtggaat aatgttttct ttgtattccc gagtcaagcg cagcgcatat tttaacaaac      7648
taaccatctt gtaagttagt ttcatttaat gcaactttat ccataatat attatgtata      7708 gcacgtcaaa aattaacaat gcgcgcgttg tcgcatctca acacgactat gatagagatc      7768
aaataaaacg cgaactaaat agcttgcgac gtaacgtgca cgatatgtgc acgcgttcag      7828
gcacgagttt tgattgtaac aagtttctac gcagcgatga catgaccccc gtagtgacaa      7888
cgatcacgcc caaagaact gccgactaca aaattaccga gtacgtcagt gacgttaaaa      7948
ctattaagcc atccaatcga ccgttagtcg aatcgggacc gctggtgcaa gaagccgcga      8008
aatatggcag atgcaccgta taacgtgtgg agtcctctca ttagcgcgtc atgtttagac      8068
aagaaagcta catatttaat tgatcccgat gattttattg ataaattgac cctaactcca      8128
tacacggtat tctacaatgg cggggttttg gttaaaattt ccggactgcg attgtacatg      8188
ctgttaacgg ctccgcccac tattaatgca attaaaaatt ccaattttaa aaaacgcagc      8248
aaaagaaaca tttgtatgaa agaatgcgta gaaggaaaaa ataatgtcgt cgacatgctg      8308
aacagcaaga tcaatatgcc tccgtgcata caaaaaatat tgggcgattt gaaaaaaaac      8368
aatgtaccgc gcggcggtat gtacaggaag aggtttatac taaactgtta cattgcaaac      8428
gtggtttcgt gtaccaaatg tgaaaaccga tgtttgatca aggctctgac acatttttac      8488
aattacgact ccaagtgtgt gggtgaagtc atgcatcttt taatcaaatc ccaagatgtg      8548
tataaaccac caaactgcca aaaaatgaaa actgtcgaca agctctgtcc gtttgctggc      8608
aactgcaagg gcctcaatcc tatttgtaat tattgaacaa taaaacaatt ataaatgtca      8668
aatttgtttt ttattaacga tacaaatgga aataataacc atctcgcaaa taaataagta      8728
ttttactgtt ttcgtaacag ttttgtaata aaaaaaccta taaat                     8773
```

<210> SEQ ID NO 5
<211> LENGTH: 357
<212> TYPE: PRT
<213> ORGANISM: Artificial sequence
<220> FEATURE:
<223> OTHER INFORMATION: Synthetic construct

<400> SEQUENCE: 5

Met Lys Lys Arg Thr Leu Arg Lys Asn Asp Arg Lys Lys Arg Met Tyr
1               5                   10                  15

Asn Met Met Glu Thr Glu Leu Lys Pro Pro Gly Pro Gln Gln Thr Ser
            20                  25                  30

Gly Gly Gly Gly Gly Asn Ser Thr Ala Ala Ala Ala Gly Gly Asn Gln
        35                  40                  45

Lys Asn Ser Pro Asp Arg Val Lys Arg Pro Met Asn Ala Phe Met Val
    50                  55                  60

Trp Ser Arg Gly Gln Arg Arg Lys Met Ala Gln Glu Asn Pro Lys Met
65                  70                  75                  80

```
His Asn Ser Glu Ile Ser Lys Arg Leu Gly Ala Glu Trp Lys Leu Leu
                85                  90                  95

Ser Glu Thr Glu Lys Arg Pro Phe Ile Asp Glu Ala Lys Arg Leu Arg
            100                 105                 110

Ala Leu His Met Lys Glu His Pro Asp Tyr Lys Tyr Arg Pro Arg Arg
        115                 120                 125

Lys Thr Lys Thr Leu Met Lys Lys Asp Lys Tyr Thr Leu Pro Gly Gly
130                 135                 140

Leu Leu Ala Pro Gly Gly Asn Ser Met Ala Ser Gly Val Gly Val Gly
145                 150                 155                 160

Ala Gly Leu Gly Ala Gly Val Asn Gln Arg Met Asp Ser Tyr Ala His
                165                 170                 175

Met Asn Gly Trp Ser Asn Gly Ser Tyr Ser Met Met Gln Asp Gln Leu
            180                 185                 190

Gly Tyr Pro Gln His Pro Gly Leu Asn Ala His Gly Ala Ala Gln Met
        195                 200                 205

Gln Pro Met His Arg Tyr Asp Val Ser Ala Leu Gln Tyr Asn Ser Met
    210                 215                 220

Thr Ser Ser Gln Thr Tyr Met Asn Gly Ser Pro Thr Tyr Ser Met Ser
225                 230                 235                 240

Tyr Ser Gln Gln Gly Thr Pro Gly Met Ala Leu Gly Ser Met Gly Ser
                245                 250                 255

Val Val Lys Ser Glu Ala Ser Ser Ser Pro Pro Val Val Thr Ser Ser
            260                 265                 270

Ser His Ser Arg Ala Pro Cys Gln Ala Gly Asp Leu Arg Asp Met Ile
        275                 280                 285

Ser Met Tyr Leu Pro Gly Ala Glu Val Pro Glu Pro Ala Ala Pro Ser
290                 295                 300

Arg Leu His Met Ser Gln His Tyr Gln Ser Gly Pro Val Pro Gly Thr
                305                 310                 315                 320

Ala Ile Asn Gly Thr Leu Pro Leu Ser His Met Ser Arg Leu Val Pro
            325                 330                 335

Arg Gly Ser Gly Ser Gly Ser Gly Leu Arg Met Gly Gly Ser His His
        340                 345                 350

His His His His Gly
        355

<210> SEQ ID NO 6
<211> LENGTH: 8536
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (8)..(841)
<223> OTHER INFORMATION:

<400> SEQUENCE: 6 agatctt atg aag aaa cgc acc ttg cgc aag aac gac cgc aag aag cgc        49
        Met Lys Lys Arg Thr Leu Arg Lys Asn Asp Arg Lys Lys Arg
        1               5                   10 atg agt aaa gga gaa gaa ctt ttc act gga gtt gtc cca att ctt gtt        97
Met Ser Lys Gly Glu Glu Leu Phe Thr Gly Val Val Pro Ile Leu Val
15                  20                  25                  30 gaa tta gat ggt gat gtt aat ggg cac aaa ttt tct gtc agt gga gag       145
Glu Leu Asp Gly Asp Val Asn Gly His Lys Phe Ser Val Ser Gly Glu
                35                  40                  45
```

```
ggt gaa ggt gat gca aca tac gga aaa ctt acc ctt aaa ttt att tgc    193
Gly Glu Gly Asp Ala Thr Tyr Gly Lys Leu Thr Leu Lys Phe Ile Cys
         50                  55                  60 act act gga aaa cta cct gtt cca tgg cca aca ctt gtc act act ttc    241
Thr Thr Gly Lys Leu Pro Val Pro Trp Pro Thr Leu Val Thr Thr Phe
         65                  70                  75 ggt tat ggt gtt caa tgc ttt gcg aga tac cca gat cat atg aaa cag    289
Gly Tyr Gly Val Gln Cys Phe Ala Arg Tyr Pro Asp His Met Lys Gln
         80                  85                  90 cat gac ttt ttc aag agt gcc atg cct gaa ggt tat gta cag gaa aga    337
His Asp Phe Phe Lys Ser Ala Met Pro Glu Gly Tyr Val Gln Glu Arg
 95             100                 105                 110 act ata ttt ttc aaa gat gac ggg aac tac aag aca cgt gct gaa gtc    385
Thr Ile Phe Phe Lys Asp Asp Gly Asn Tyr Lys Thr Arg Ala Glu Val
                115                 120                 125 aag ttt gaa ggt gat acc ctt gtt aat aga atc gag tta aaa ggt att    433
Lys Phe Glu Gly Asp Thr Leu Val Asn Arg Ile Glu Leu Lys Gly Ile
                130                 135                 140 gat ttt aaa gaa gat gga aac att ctt gga cac aaa ttg gaa tac aac    481
Asp Phe Lys Glu Asp Gly Asn Ile Leu Gly His Lys Leu Glu Tyr Asn
            145                 150                 155 tat aac tca cac aat gta tac atc atg gca gac aaa caa aag aat gga    529
Tyr Asn Ser His Asn Val Tyr Ile Met Ala Asp Lys Gln Lys Asn Gly
        160                 165                 170 atc aaa gtt aac ttc aaa att aga cac aac att gaa gat gga agc gtt    577
Ile Lys Val Asn Phe Lys Ile Arg His Asn Ile Glu Asp Gly Ser Val
175                 180                 185                 190 caa cta gca gac cat tat caa caa aat act cca att ggc gat ggc cct    625
Gln Leu Ala Asp His Tyr Gln Gln Asn Thr Pro Ile Gly Asp Gly Pro
                195                 200                 205 gtc ctt tta cca gac aac cat tac ctg tcc aca caa tct gcc ctt tcg    673
Val Leu Leu Pro Asp Asn His Tyr Leu Ser Thr Gln Ser Ala Leu Ser
            210                 215                 220 aaa gat ccc aac gaa aag aga gac cac atg gtc ctt ctt gag ttt gta    721
Lys Asp Pro Asn Glu Lys Arg Asp His Met Val Leu Leu Glu Phe Val
        225                 230                 235 aca gct gct ggg att aca cat ggc atg gat gaa cta tac aaa tct aga    769
Thr Ala Ala Gly Ile Thr His Gly Met Asp Glu Leu Tyr Lys Ser Arg
240                 245                 250 ctg gtt ccg cgt gga tcc ggc tct gga tct ggc ctc agg atg ggg ggt    817
Leu Val Pro Arg Gly Ser Gly Ser Gly Ser Gly Leu Arg Met Gly Gly
255                 260                 265                 270 tct cat cat cat cat cat cat ggc tagatacgcg aacgccggca tcagtgcctg    871
Ser His His His His His His Gly
                275 ggccaggcct taaacacta tacattgtta ttagtacatt tattaagcgt tagattctgt    931 gcgttgttga tttacagaca attgttgtac gtattttaat aattcattaa atttgtaatc    991 tttagggtgg tatgttagag cgaaaatcaa atgattttca gcgtctttgt atctgaattt    1051 aaatattaaa tcctcaatag atttgtaaaa taggtttcga ttggtttcaa acaagggttg    1111 tttttgcaaa ccgatggctg gactatctaa tggattttcg ctcaacacca cacgacttgc    1171 caaatcttgt agcagcaatc tagctttgtc gatattcgtt tgtgttttgt tttgtaataa    1231 agattcgacg tcgttcaaaa tattatgcgc ttttgtattt ttttcatcac tgtcgttggt    1291 gtacaattga ctcgacgtaa acacgttaaa taaagcttgg acatatttaa catcgggcgc    1351 gttaggccga ttattgccgc cgtcgtccca accctcgtcg ttagaagttg cttccgaaga    1411 cgattttgcc atagccacac gacgcctatt aattgtgtcg actaacacgt ccgcgatcaa    1471
```

```
attttttagtt gttgagttttt tcggaattat ttctgattgc ggacgttttt gtgcgggttt    1531
caatctaact gtgcccgatt ttaattcaga caacacgtta gaaagcgatg gtgcaggcgg    1591
tggtaacatt tcagccggca aatctactaa tggcggctgt aatggagctg atgataaatc    1651
tatcattggt ggaggcgcag gcggggctgg cggcggaggt ggtggcggcg gtgatgcaga    1711
cggcggtttg ggctctttag gcaacacagt cgtcggcacc tcaattattg tattggtttc    1771
gggcgccgtt tttggtttga ccggtctgag acgagtgcga ttttttttcgt ttctaatagc    1831 ttccaacaat tgttgtctgt cgtctaaagg tgcagcgggt tgaggtttag tcggcattgg    1891
tggagcgggc ggcaattcag acatcgatga tggcggtggt ggtggtggag gtggaggcgc    1951
tggaatgtta ggcacggaag aaggtggtgg cggtgccgcc ggtattataa tttgttctgg    2011
tttagtttgt tcgtgcacga ttgtgggcac cggcgcaggc gccgctggct gcacaacgga    2071
aggtcgtctg cttcgaggca gcgcttgggg tggtggcggc ggcaattcaa tattataatt    2131
ggaatacaaa tcgtaaaaat ctgctataag cattgtaatt tcgctatcgt ttaccgtgcc    2191
gatatttaac aatcgctcaa tgtaagcaat tgtattgtag agggattgtc tcaagctcgg    2251
atcccgcacg ttgatgacaa gccttttcat ttttaccaca gcattgtagt agcgagacac    2311
ttcgctgtcg tcgacgtaca tgtacgcttt gttgtcaaaa acgtcgttgg caaactttaa    2371
aatatttaaa aaaacatctc tgttcagcaa cactgtgttg tcgtaaatgc tgtctttgat    2431
aatttgcgct tccgcagtat cgacgcgttc aaaaaattga tgtgcatcaa ttttattgtt    2491
cctattattg aataaataag attgtacaga ttcatattta cgattcgtca tggccaccac    2551
caccgccaca aatgctacgc tgcaaacgct ggtacaattt tacgaaaact gcaaaaacgt    2611
caaaactcgg tataaaataa tcaacgggcg ttttggcaaa atatctattt tatcgcacaa    2671
gcccactagc aaattgtatt tgcagaaaac aatttcggcg cacaatttta acgtcgacga    2731
aataaaagtc caccagttaa tgaacgacca cccaaatttt ataaaaatct attttaatca    2791
cggtttcatt aacaaccaag tgatcgtgat ggactacatc gactgtccgg atttatttga    2851
aacgctacaa attaaaggcg agctttcgca ccaacttgtt agcaatatta ttagacaact    2911
gtgtgaagcg ctcaacgatt tgcacaaaca caatttcata cacaacgaca taaaactcga    2971
aaatgtctta tatttcgaag cactcgatcg cgtgtatgtt tgcgattacg gattgtgcaa    3031
acacgaaaac ttacccagcg tgcacgacgg cacgttggag tattttagtc cggaaaaaat    3091
tcgacgccac aactatgcac gttcgtttga ctggtacgcc gtcggcgtgt aacgtacaa    3151 gttgctaacc ggcggccgac acccgtttga aaaagcgaa gacgaaatgt tggacttgaa    3211
tagcatgaag cgtcgtcagc aatacaacga cattggtgtt ttaaaacacg ttcgtaacgt    3271
taacgctcgt gactttgtgt actgcctaac aagatacaac ctagattgta gactaacaaa    3331
ttacaaacaa attataaaac atgagttttt gtcgtgagtg gtgttaataa aaatcataaa    3391
aattattgta aatgttttatt atttaaaaac gattcaaata tataataaaa acaatctaca    3451
tctatttctt cacaatccat aacacacaac aggtccatca atgagttttt gtctttatct    3511
gacatactat gtgcatgtaa caaatcaaat acatcttta atctctata cacatctata    3571 cattgtctac caaaatcttt aataactgta taacatgaaa aagacttttc ttcttgcgtg    3631
gttttgccgc gtagatattg aaataaaatg tgcatgcaag cttggcactg gccgtcgttt    3691
tacaacgtcg tgactgggaa aaccctggcg ttacccaact taatcgcctt gcagcacatc    3751
cccctttcgc cagctggcgt aatagcgaag aggcccgcac cgatcgccct tcccaacagt    3811
tgcgcagcct gaatggcgaa tggaaattgt aagcgttaat attttgttaa aattcgcgtt    3871
```

```
aaatttttgt taaatcagct catttttttaa ccaataggcc gaaatcggca aaatccctta    3931
taaatcaaaa gaatagaccg atatagggtt gagtgttgtt ccagtttgga acaagagtcc    3991
actattaaag aacgtggact ccaacgtcaa agggcgaaaa accgtctatc agggcgatgg    4051
cccactacgt gaaccatcac cctaatcaag ttttttgggg tcgaggtgcc gtaaagcact    4111
aaatcggaac cctaaaggga gcccccgatt tagagcttga cggggaaagc ggcgaacgt    4171 ggcgagaaag gaagggaaga aagcgaaagg agcgggcgct agggcgctgg caagtgtagc    4231
ggtcacgctg cgcgtaacca ccacacccgc cgcgcttaat gcgccgctac agggcgcgtc    4291
aggtggcact tttcggggaa atgtgcgcgg aaccccctatt tgtttatttt tctaaataca    4351
ttcaaatatg tatccgctca tgagacaata accctgataa atgcttcaat aatattgaaa    4411
aaggaagagt atgagtattc aacatttccg tgtcgccctt attccctttt ttgcggcatt    4471
ttgccttcct gttttgctc acccagaaac gctggtgaaa gtaaagatg ctgaagatca    4531 gttgggtgca cgagtgggtt acatcgaact ggatctcaac agcggtaaga tccttgagag    4591
ttttcgcccc gaagaacgtt ttccaatgat gagcactttt aaagttctgc tatgtggcgc    4651
ggtattatcc cgtattgacg ccgggcaaga gcaactcggt cgccgcatac actattctca    4711
gaatgacttg gttgagtact caccagtcac agaaaagcat cttacggatg gcatgacagt    4771
aagagaatta tgcagtgctg ccataaccat gagtgataac actgcggcca acttacttct    4831
gacaacgatc ggaggaccga aggagctaac cgcttttttg cacaacatgg gggatcatgt    4891
aactcgcctt gatcgttggg aaccggagct gaatgaagcc ataccaaacg acgagcgtga    4951
caccacgatg cctgtagcaa tggcaacaac gttgcgcaaa ctattaactg gcgaactact    5011
tactctagct tcccggcaac aattaataga ctggatggag gcggataaag ttgcaggacc    5071
acttctgcgc tcggcccttc cggctggctg gtttattgct gataaatctg gagccggtga    5131
gcgtgggtct cgcggtatca ttgcagcact ggggccagat ggtaagccct cccgtatcgt    5191
agttatctac acgacgggga gtcaggcaac tatggatgaa cgaaatagac agatcgctga    5251
gataggtgcc tcactgatta agcattggta actgtcagac caagtttact catatatact    5311
ttagattgat ttaaaacttc attttttaatt taaaaggatc taggtgaaga tcctttttga    5371
taatctcatg accaaaatcc cttaacgtga gttttcgttc cactgagcgt cagaccccgt    5431
agaaaagatc aaaggatctt cttgagatcc tttttttctg cgcgtaatct gctgcttgca    5491
aacaaaaaaa ccaccgctac cagcggtggt ttgtttgccg gatcaagagc taccaactct    5551
ttttccgaag gtaactggct tcagcagagc gcagatacca aatactgttc ttctagtgta    5611
gccgtagtta ggccaccact tcaagaactc tgtagcaccg cctacatacc tcgctctgct    5671
aatcctgtta ccagtggctg ctgccagtgg cgataagtcg tgtcttaccg ggttggactc    5731
aagacgatag ttaccggata aggcgcagcg gtcgggctga acggggggt cgtgcacaca    5791 gcccagcttg gagcgaacga cctacaccga actgagatac ctacagcgtg agctatgaga    5851
aagcgccacg cttcccgaag ggagaaaggc ggacaggtat ccggtaagcg cagggtcgg    5911 aacaggagag cgcacgaggg agcttccagg gggaaacgcc tggtatcttt atagtcctgt    5971
cgggtttcgc cacctctgac ttgagcgtcg attttttgtga tgctcgtcag ggggggcggag    6031 cctatggaaa aacgccagca acgcggcctt tttacggttc ctggccttt gctgccttt    6091 tgctcacatg ttctttcctg cgttatcccc tgattctgtg ataaccgta ttaccgcctt    6151 tgagtgagct gataccgctc gccgcagccg aacgaccgag cgcagcgagt cagtgagcga    6211
ggaagcggaa gagcgcccaa tacgcaaacc gcctctcccc gcgcgttggc cgattcatta    6271
```

-continued

```
atgcagctgg cacgacaggt ttcccgactg gaaagcgggc agtgagcgca acgcaattaa      6331
tgtgagttag ctcactcatt aggcacccca ggctggccgc aattcagaga aaccagtcgc      6391
cgcgtcaagt ttgtagtctg gccgatcttg aacagattcc tttcggcgta cagcagcgtc      6451
gtggccgcat agaaatggcc ctcgacggga gcggaattaa actttactgt cgcttgggcg      6511
tcttggagca ggctcaacgc cgactgtcgg gcggtgcact ggggcaacac gtgttcgtaa      6571
aaccaatttt gcagctccgc cgcgttggtc atcttggagc gcatgaacaa ctgtataacg      6631
cctattttgt cgagtaatat tgtttgcgtc tgcaaataca gcggattgcc ttgtttaacg      6691
tgtttttctt tgctgatatt aatacacgct tgctcgaatg tgcatttgta cttgccgtcg      6751
acgtgatctc taattgcttt tttggtgttt ttaaatttta atttgtttgc aatgtccctg      6811
gccacaaatc tgaccggctg ctcgccgccg agcacgtacc tcagcgtgaa cgtgtcttca      6871
ccgaatttga acttgccaat tttaacttga gccattttt atttacaaac tacgcgtaga      6931
gattcgacga aagcgcaaaa caaactgaga acaactagta gtggtgttgc tacaaattcc      6991
ctccggcgtt gatgcgctgc acttcaaata gttcgttgac gccctcctcc gtttcgccaa      7051
acacgtccaa cgggtggtcg ataaccagca gcgtgccgca cgcaacgcac aagtatctgt      7111
acaccgaatg atcgtcgggc gaaggcacgt cggcctccaa gtggcaatat tggcaaattc      7171
gaaaatatat acaattgggt tgtttgcgca tatctatcgt ggcgttgggc atgtacgtct      7231
gaacgttgat ttgcatgcaa gccgaaatta aatcattgcg attaatgcga ttaaaacgtt      7291
gtacatcctc gttttttaatc atgccgtcga ttagatcgcg caatcgagtc aagtggtcaa      7351
agtgtggaat aatgttttct ttgtattccc gagtcaagcg cagcgcatat tttaacaaac      7411
taaccatctt gtaagttagt ttcatttaat gcaactttat ccataatat attatgtata      7471
gcacgtcaaa aattaacaat gcgcgcgttg tcgcatctca acacgactat gatagagatc      7531
aaataaaacg cgaactaaat agcttgcgac gtaacgtgca cgatatgtgc acgcgttcag      7591
gcacgagttt tgattgtaac aagtttctac gcagcgatga catgaccccc gtagtgacaa      7651
cgatcacgcc caaagaact gccgactaca aaattaccga gtacgtcagt gacgttaaaa      7711
ctattaagcc atccaatcga ccgttagtcg aatcgggacc gctggtgcaa gaagccgcga      7771
aatatggcag atgcaccgta taacgtgtgg agtcctctca ttagcgcgtc atgtttagac      7831
aagaaagcta catatttaat tgatcccgat gattttattg ataaattgac cctaactcca      7891
tacacggtat tctacaatgg cggggttttg gttaaaattt ccggactgcg attgtacatg      7951
ctgttaacgg ctccgcccac tattaatgca attaaaaatt ccaattttaa aaaacgcagc      8011
aaaagaaaca tttgtatgaa agaatgcgta gaaggaaaaa ataatgtcgt cgacatgctg      8071
aacagcaaga tcaatatgcc tccgtgcata caaaaaatat tgggcgattt gaaaaaaaac      8131
aatgtaccgc gcggcggtat gtacaggaag aggtttatac taaactgtta cattgcaaac      8191
gtggtttcgt gtaccaaatg tgaaaaccga tgtttgatca aggctctgac acattttac      8251
aattacgact ccaagtgtgt gggtgaagtc atgcatcttt taatcaaatc ccaagatgtg      8311
tataaaccac caaactgcca aaaaatgaaa actgtcgaca agctctgtcc gtttgctggc      8371
aactgcaagg gcctcaatcc tatttgtaat tattgaacaa taaaacaatt ataaatgtca      8431
aatttgtttt ttattaacga tacaaatgga aataataacc atctcgcaaa taataagta      8491
ttttactgtt ttcgtaacag ttttgtaata aaaaaaccta taaat                     8536
```

<210> SEQ ID NO 7
<211> LENGTH: 278
<212> TYPE: PRT

```
<213> ORGANISM: Artificial sequence
<220> FEATURE:
<223> OTHER INFORMATION: Synthetic construct

<400> SEQUENCE: 7

Met Lys Lys Arg Thr Leu Arg Lys Asn Asp Lys Lys Arg Met Ser
1               5                   10                  15

Lys Gly Glu Glu Leu Phe Thr Gly Val Val Pro Ile Leu Val Glu Leu
            20                  25                  30

Asp Gly Asp Val Asn Gly His Lys Phe Ser Val Ser Gly Glu Gly Glu
            35                  40                  45

Gly Asp Ala Thr Tyr Gly Lys Leu Thr Leu Lys Phe Ile Cys Thr Thr
    50                  55                  60

Gly Lys Leu Pro Val Pro Trp Pro Thr Leu Val Thr Thr Phe Gly Tyr
65                  70                  75                  80

Gly Val Gln Cys Phe Ala Arg Tyr Pro Asp His Met Lys Gln His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
            115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Val Asn Phe Lys Ile Arg His Asn Ile Glu Asp Gly Ser Val Gln Leu
            180                 185                 190

Ala Asp His Tyr Gln Gln Asn Thr Pro Ile Gly Asp Gly Pro Val Leu
            195                 200                 205

Leu Pro Asp Asn His Tyr Leu Ser Thr Gln Ser Ala Leu Ser Lys Asp
    210                 215                 220

Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Ser Arg Leu Val
                245                 250                 255

Pro Arg Gly Ser Gly Ser Gly Ser Gly Leu Arg Met Gly Gly Ser His
            260                 265                 270

His His His His Gly
            275
```